(12) United States Patent
Bierman

(10) Patent No.: US 11,627,766 B2
(45) Date of Patent: Apr. 18, 2023

(54) LUMBAR SUPPORTIVE WETSUIT

(71) Applicant: Steven F. Bierman, Del Mar, CA (US)

(72) Inventor: Steven F. Bierman, Del Mar, CA (US)

( * ) Notice: Subject to any disclaimer, the term of this patent is extended or adjusted under 35 U.S.C. 154(b) by 132 days.

(21) Appl. No.: 16/635,921

(22) PCT Filed: Sep. 21, 2018

(86) PCT No.: PCT/US2018/052271
§ 371 (c)(1),
(2) Date: Jan. 31, 2020

(87) PCT Pub. No.: WO2019/060763
PCT Pub. Date: Mar. 28, 2019

(65) Prior Publication Data
US 2020/0229518 A1    Jul. 23, 2020

Related U.S. Application Data

(60) Provisional application No. 62/562,245, filed on Sep. 22, 2017.

(51) Int. Cl.
*A41D 13/012* (2006.01)
*A41D 13/05* (2006.01)

(52) U.S. Cl.
CPC ....... *A41D 13/012* (2013.01); *A41D 13/0525* (2013.01)

(58) Field of Classification Search
None
See application file for complete search history.

(56) References Cited

U.S. PATENT DOCUMENTS

| | | | | |
|---|---|---|---|---|
| 1,447,904 A | * | 3/1923 | Sinclair | A61F 5/03 450/155 |
| 1,866,200 A | * | 7/1932 | Feir | B63C 9/105 441/88 |
| 1,930,034 A | * | 10/1933 | Bergh | A41D 7/00 2/67 |
| 1,932,270 A | * | 10/1933 | Hoier | A61F 5/03 450/119 |

(Continued)

FOREIGN PATENT DOCUMENTS

| | | |
|---|---|---|
| EP | 0 636 325 A2 | 2/1995 |
| FR | 2 788 945 A1 | 8/2000 |

(Continued)

OTHER PUBLICATIONS

International Search Report and Written Opinion dated Jan. 18, 2019 for application No. PCT/US2018/52271 filed Sep. 21, 2018.

(Continued)

*Primary Examiner* — Jocelyn Bravo
(74) *Attorney, Agent, or Firm* — Knobbe Martens Olson & Bear, LLP

(57) ABSTRACT

The present disclosure relates to a wetsuit that provides support for the lumbosacral region of the wearer. The wetsuit has at least one layer of foam rubber or other wetsuit material with a lumbar portion disposed in the lumbosacral region of the wearer. In certain embodiments, the wetsuit has at least one tensioning mechanism that allows the wearer to selectively change a level of support provided by the lumbar portion to the lumbosacral region of the wearer.

24 Claims, 34 Drawing Sheets

(56) References Cited

U.S. PATENT DOCUMENTS

| | | | | |
|---|---|---|---|---|
| 1,965,213 A * | 7/1934 | Bernstein | A41B 9/08 | 2/79 |
| 1,981,320 A * | 11/1934 | Martin | A41D 7/00 | 2/67 |
| 2,181,689 A * | 11/1939 | Bell | A61F 5/028 | 602/19 |
| 2,219,475 A * | 10/1940 | Flaherty | A61F 13/143 | 602/19 |
| 2,280,274 A * | 4/1942 | Wildermuth | A61H 1/008 | 606/237 |
| 2,730,096 A * | 1/1956 | Pease | A61F 5/028 | 602/19 |
| 2,900,984 A * | 8/1959 | Cunningham | A41C 1/00 | 450/132 |
| 3,362,402 A * | 1/1968 | Loeffel | A61F 5/26 | 602/19 |
| 3,434,469 A * | 3/1969 | Swift | A61F 5/028 | 602/19 |
| 3,452,748 A * | 7/1969 | Caprio | A61F 5/028 | 602/19 |
| 3,570,480 A * | 3/1971 | Stubbs | A61F 5/03 | 602/19 |
| 3,710,801 A * | 1/1973 | Bienenfeld | A41C 1/02 | 450/123 |
| 3,717,143 A * | 2/1973 | Johnson | A61F 5/028 | 602/19 |
| 4,175,553 A * | 11/1979 | Rosenberg | A61F 5/028 | 602/19 |
| 4,245,628 A * | 1/1981 | Eichler | A61F 5/028 | 602/19 |
| 4,475,543 A * | 10/1984 | Brooks | A61L 15/07 | 602/19 |
| 4,622,957 A * | 11/1986 | Curlee | A61F 5/34 | 128/118.1 |
| 4,633,526 A * | 1/1987 | Richardson | A41D 13/0125 | 2/2.14 |
| D296,930 S * | 7/1988 | Carabelli | D24/190 | |
| 4,820,221 A * | 4/1989 | Aubrey | A61F 5/02 | 441/106 |
| 4,936,805 A * | 6/1990 | Piatt, Jr. | A41D 13/0531 | 441/106 |
| 5,062,414 A * | 11/1991 | Grim | A61F 7/007 | 602/19 |
| 5,086,758 A * | 2/1992 | Schiek, Sr. | A61F 5/028 | 128/876 |
| 5,105,474 A * | 4/1992 | Skinner | A41D 13/0575 | 2/2.17 |
| 5,105,806 A * | 4/1992 | Woodhouse | A61F 5/028 | 128/112.1 |
| 5,122,111 A * | 6/1992 | Sebastian | A61F 5/028 | 128/108.1 |
| 5,207,635 A * | 5/1993 | Richards | A61F 5/028 | 128/876 |
| 5,267,947 A * | 12/1993 | James | A61F 5/028 | 2/311 |
| 5,274,851 A * | 1/1994 | Simpkins, Sr. | A61F 5/028 | 2/102 |
| 5,328,398 A * | 7/1994 | Aubrey | B63H 8/56 | 441/106 |
| 5,375,279 A * | 12/1994 | Toso | A47C 16/00 | 5/633 |
| 5,402,539 A * | 4/1995 | Hewitt | A62B 17/001 | 2/227 |
| 5,429,587 A * | 7/1995 | Gates | A61F 5/028 | 128/876 |
| 5,533,961 A * | 7/1996 | Iwata | A41D 13/0525 | 602/19 |
| 5,551,085 A * | 9/1996 | Leighton | A61F 5/028 | 2/44 |
| 5,611,084 A * | 3/1997 | Garry | A41D 13/0525 | 2/102 |
| 5,628,721 A * | 5/1997 | Arnold | A61F 5/028 | 128/118.1 |
| 5,643,184 A * | 7/1997 | Toso | A47C 16/00 | 2/44 |
| 5,651,763 A * | 7/1997 | Gates | A61F 5/028 | 128/876 |
| 5,728,055 A * | 3/1998 | Sebastian | A61F 5/012 | 128/100.1 |
| 5,857,947 A * | 1/1999 | Dicker | A63B 21/4019 | 482/124 |
| 5,897,423 A * | 4/1999 | Rosenberg | A41C 1/10 | 450/115 |
| 5,954,557 A * | 9/1999 | Mariani | A61F 5/028 | 441/106 |
| 6,108,819 A * | 8/2000 | DeBaene | A41D 1/067 | 2/227 |
| 6,213,968 B1 * | 4/2001 | Heinz | A61F 5/028 | 602/19 |
| 6,332,221 B1 * | 12/2001 | Gracey | A41D 13/0531 | 2/69 |
| 6,419,652 B1 * | 7/2002 | Slautterback | A61F 5/028 | 128/96.1 |
| 7,252,625 B1 * | 8/2007 | Perka | A41D 13/0525 | 2/2.15 |
| 7,364,558 B2 * | 4/2008 | Weaver, II | A61F 5/028 | 297/230.1 |
| 8,118,762 B2 * | 2/2012 | Bort | A61F 5/0109 | 602/23 |
| 8,398,170 B2 * | 3/2013 | Walker | A47C 7/425 | 297/284.3 |
| 8,904,568 B2 * | 12/2014 | Fruscione-Loizides | A41C 1/10 | 2/312 |
| 9,439,460 B2 * | 9/2016 | Richards | A62B 35/00 | |
| 10,212,974 B1 * | 2/2019 | Joshi | A41D 13/0537 | |
| 10,617,553 B2 * | 4/2020 | Reed | A61F 5/055 | |
| 10,906,619 B2 * | 2/2021 | Kreijkamp | B63H 8/58 | |
| 11,019,854 B1 * | 6/2021 | Lee | A41D 27/20 | |
| 2001/0008955 A1 * | 7/2001 | Garth | A61F 5/028 | 602/19 |
| 2003/0135134 A1 * | 7/2003 | Chase | A61F 5/028 | 600/595 |
| 2003/0212355 A1 * | 11/2003 | Shilling | A61F 5/026 | 602/19 |
| 2004/0077981 A1 * | 4/2004 | Weaver, II | A61F 5/028 | 602/19 |
| 2004/0078876 A1 * | 4/2004 | Wilson | A41D 13/0002 | 2/458 |
| 2005/0005337 A1 * | 1/2005 | Yokoyama | B63C 11/04 | 2/2.15 |
| 2005/0177920 A1 * | 8/2005 | Wilkinson | A41F 9/025 | 2/69 |
| 2005/0197607 A1 * | 9/2005 | Brown | A61F 5/3746 | 602/19 |
| 2006/0130215 A1 * | 6/2006 | Torry | A41D 13/065 | 2/227 |
| 2009/0031478 A1 * | 2/2009 | Conolly | A41D 13/0015 | 2/267 |
| 2009/0105626 A1 * | 4/2009 | Lemons | A61F 15/008 | 602/61 |
| 2009/0138064 A1 * | 5/2009 | Horn | A61F 5/026 | 607/108 |
| 2011/0054373 A1 * | 3/2011 | Reiley | A61F 5/02 | 602/19 |
| 2011/0131697 A1 * | 6/2011 | Kawahara | A61F 5/01 | 2/44 |
| 2012/0144541 A1 * | 6/2012 | Mitchell | B63C 11/04 | 2/2.15 |
| 2012/0174852 A1 * | 7/2012 | Greenstone | G09F 21/02 | 116/173 |
| 2013/0219579 A1 * | 8/2013 | Molyneux | A41D 13/012 | 2/2.15 |
| 2015/0065933 A1 * | 3/2015 | Josefek | A61F 5/028 | 602/13 |
| 2015/0143621 A1 * | 5/2015 | Conolly | A63B 21/4011 | 2/467 |

(56) References Cited

U.S. PATENT DOCUMENTS

| | | | |
|---|---|---|---|
| 2015/0237928 A1* | 8/2015 | Molyneux | A41D 13/012 2/2.15 |
| 2015/0282974 A1* | 10/2015 | Kamenaga | A61F 5/0193 602/19 |
| 2017/0105866 A1* | 4/2017 | Ritter | A61F 5/028 |
| 2017/0245561 A1* | 8/2017 | Flockton | A41D 7/00 |
| 2017/0265531 A1* | 9/2017 | Toussaint | A41D 7/005 |
| 2017/0280792 A1* | 10/2017 | Spenser | A41D 27/02 |
| 2021/0007877 A1* | 1/2021 | Vyas | A61F 5/28 |

FOREIGN PATENT DOCUMENTS

| | | | | |
|---|---|---|---|---|
| GB | 2076654 A | * | 12/1981 | A61F 5/028 |
| GB | 2076654 A | | 12/1981 | |
| JP | 1995-088218 | | 4/1995 | |
| JP | 3127569 | | 12/2006 | |
| JP | 3164788 | | 12/2010 | |
| JP | 2011-32599 | | 2/2011 | |
| JP | 2012-82561 | | 4/2012 | |

OTHER PUBLICATIONS

Extended European Search Report dated May 28, 2021, corresponding to European Patent Application No. 18857862.9, filed on Apr. 21, 2020.

* cited by examiner

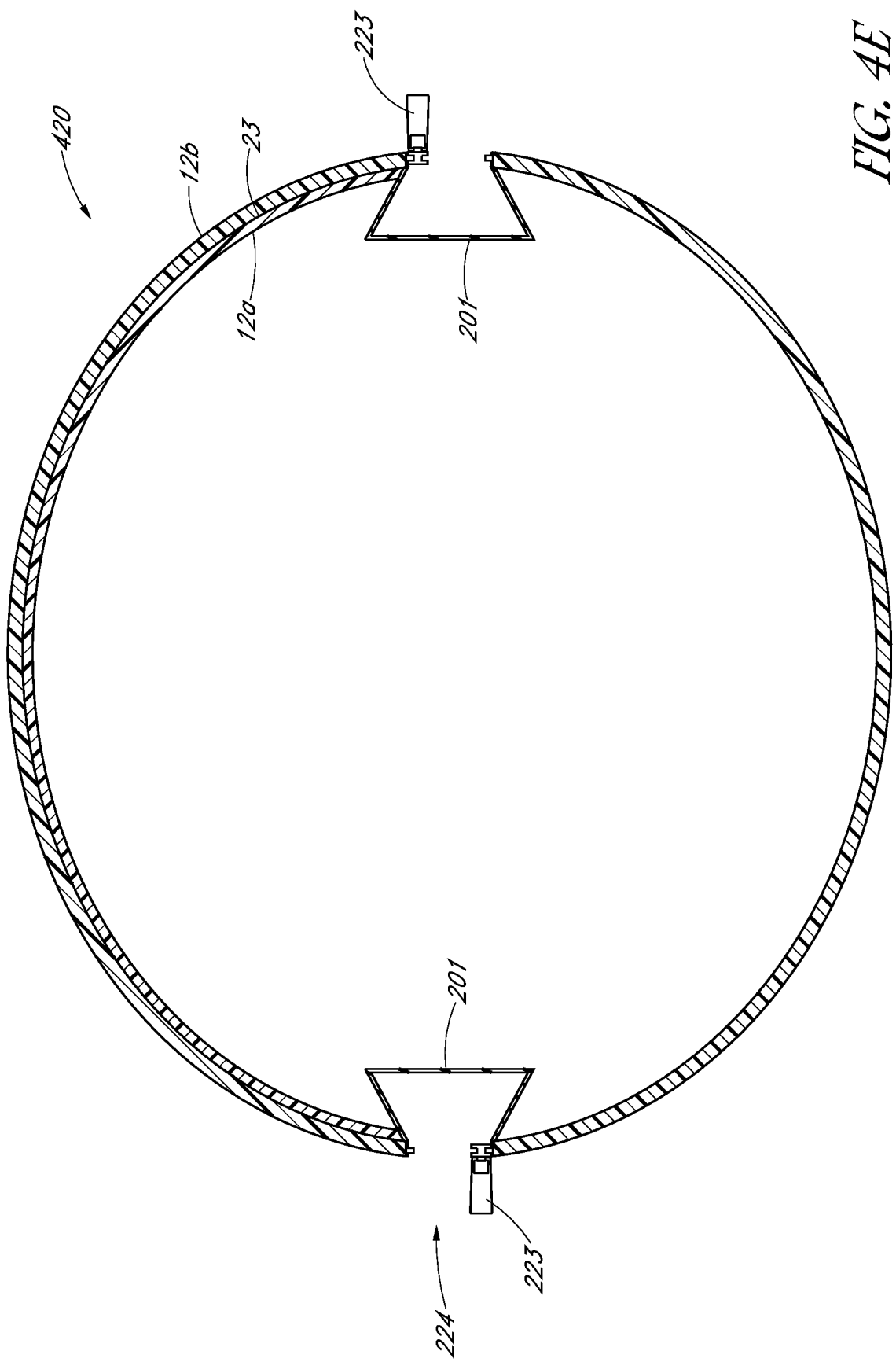

LUMBAR SUPPORTIVE WETSUIT

CROSS-REFERENCE TO RELATED APPLICATIONS

This application is a United States national stage application under 35 U.S.C. § 371 of PCT Application No. PCT/US2018/052271 designating the United States, filed on Sep. 21, 2018, which claims priority to U.S. Provisional Patent App. No. 62/562,245, filed on Sep. 22, 2017. The disclosures of the above-described applications are hereby incorporated by reference in their entireties.

BACKGROUND

Field

Embodiments of the disclosure are generally related to wetsuit having an integrated lumbar support to help alleviate back pain and other back problems or simply to provide support to prevent back problems. Embodiments are capable of being used for many different activities including water-sports like surfing as well as diving, swimming, water-polo, or other water-related activities.

Description of the Related Art

Wetsuits are tight-fitting water-permeable suits worn by divers, surfers, board sailors, swimmers, and others in order to retain body heat, protect the skin from wildlife and sharp objects such as coral or surfboard fins, and to prevent skin rashes from friction. Modern wetsuits typically consist of flexible, heat-insulative material such as elastomer foam, one example being Neoprene foam.

Various water activities can cause stress to a person's back resulting in muscle strains and other injuries. Surfing is especially stressful on the back, and many surfers suffer from chronic back pain or repeated back injury such as spinal stenosis, facet syndrome, disc herniation, sciatica, and others. The sport of surfing requires the use of many different muscle groups including back and lumbar muscles. Surfing requires extensive periods of paddling on one's stomach as well as being able to "pop-up" or move from lying on the stomach to standing. Additionally, once a surfer is standing on a wave, they may employ various maneuvers to gain speed, to guide the board to different parts of the wave, to do tricks, or to generally position them on the correct section of the wave to ensure they are able to remain on the wave. These maneuvers vary from relatively simple to highly advanced. The more advanced maneuvers can require large amounts of core and back strength, twisting, and flexion. Consequently, these maneuvers can cause large amounts of torque to be applied to the spine and the surrounding muscles and ligaments.

In addition to the aforementioned maneuvers, paddling on a surfboard and popping up also require the use of the back and lumbar muscles and can cause stress to a surfer's back. As a result, many surfers suffer from back injuries and some complain of persistent back pains caused by surfing. Additionally, many other water-related activities such as wakeboarding, kiteboarding, paddle boarding, skiing, tubing, etc. can cause significant stress to the lower back.

Although various types of wetsuits are known, most if not all wetsuits are generally flexible and provide little to no rigidity or back or lumbar support. Thus, there remains a need for improved wetsuit designs that are capable of providing lumbar and/or back support.

SUMMARY

The apparatuses and systems of the present disclosure have several features, no single one of which is solely responsible for its desirable attributes. Without limiting the scope of this invention as expressed by the claims which follow, its more prominent features will now be discussed briefly. After considering this discussion, and particularly after reading the section entitled "DETAILED DESCRIPTION OF CERTAIN PREFERRED EMBODIMENTS," one will understand how the features of this wetsuit provide several advantages over current wetsuits.

One aspect is a wetsuit that provides adjustable support to a lumbosacral region of a wearer of the wetsuit. The wetsuit comprises at least one layer of material that has a lumbar portion disposed in the lumbosacral region of the wearer. The wetsuit further includes at least one tensioning mechanism that allows the wearer to selectively change a level of support provided by the lumbar portion to the lumbosacral region of the wearer.

Another aspect is a wetsuit that provides adjustable support to a lumbosacral region of a wearer of the wetsuit. The wetsuit comprises at least one layer of foam rubber that has a lumbar portion disposed in the lumbosacral region of the wearer, a slot, a fastener, and a barrier panel. The slot defines an opening in the at least one layer of foam rubber and has a first edge and a second edge. The fastener is configured to close the opening by moving from an open position to a closed position. A level of support provided by the lumbar portion to the lumbosacral region of the wearer is greater when the opening is closed than when the opening is open. The barrier panel attaches to the first edge and the second edge and underlies the slot so as to inhibit liquid from entering the wetsuit when the fastener is at least in the open position.

Another aspect is a wetsuit that provides adjustable support to a lumbosacral region of a wearer of the wetsuit. The wetsuit comprises at least one layer of foam rubber and a lumbar portion adjacent to the at least one layer of foam rubber. The lumbar portion extends around at least a portion of a torso of the wearer. The lumbar portion has an elastic strap so that the wearer of the wetsuit can selectively change a level of support provided by the lumbar portion to the lumbosacral region of the wearer.

Another aspect is a wetsuit that is configured to provide support to a lumbosacral region of a wearer of the wetsuit. The wetsuit comprises at least one layer of foam rubber that has a lumbar portion disposed in the lumbosacral region of the wearer.

BRIEF DESCRIPTION OF THE DRAWINGS

FIG. 4E is a horizontal cross-sectional view through the lumbar portion taken along line 4E-4E of the wetsuit in FIG. 4D.

DETAILED DESCRIPTION OF CERTAIN PREFERRED EMBODIMENTS

Any feature or combination of features described herein are included within the scope of the present disclosure provided that the features included in any such combination are not mutually inconsistent as will be apparent from the context, this description, and the knowledge of one skilled in the art. For example, features from the different embodiments of the wetsuit can be combined to form another embodiment which will also fall within the scope of the present disclosure. In addition, any feature or combination of features can be specifically excluded from any embodiment of the present disclosure. For purposes of summarizing the present disclosure, certain aspects, advantages, and novel features of the present disclosure are described herein. Of course, not necessarily all such aspects, advantages, or features will be present in any particular embodiment of the present disclosure.

Embodiments presented herein are by way of example and not by way of limitation. The intent of the following detailed description, although discussing exemplary embodiments, is to be construed to cover all modifications, alternatives, and equivalents of the embodiments as may fall within the spirit and scope of the disclosure.

Embodiments of the present disclosure relate to a lumbar supportive wetsuit. Embodiments of the wetsuit can comprise an integrated back and/or lumbar support. Certain embodiments are capable of providing pressure against the lumbosacral and/or paravertebral lumbar area. Some embodiments are capable of providing increased rigidity and support for the lumbosacral and/or paravertebral lumbar area. This pressure and/or support can ease the strain on the muscles in that region while a person is engaged in water-related activities. By easing the muscle strain, embodiments that fall within this disclosure may reduce the risk of back injuries and may enable people to recover from persistent back injuries without having to cease their water-related activities for an extended period of time. Further, a lumbar supportive wetsuit can be useful in activities that are not as stressful on a person's back, because it may still be beneficial to have back support if the person has an existing back problem.

Figure 1A:
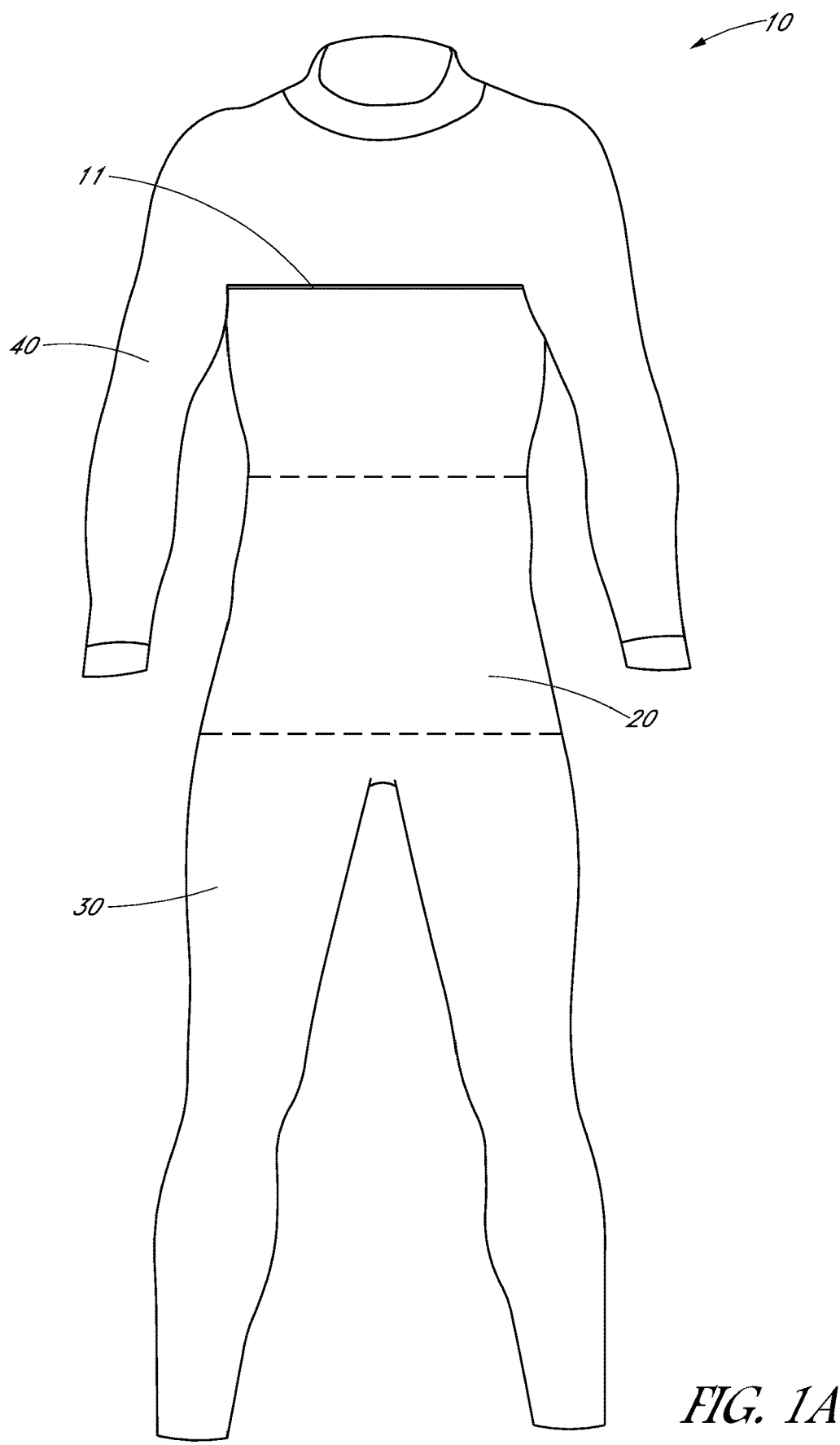
FIG. 1A is a front view of a wetsuit with a lumbar support features according to a preferred embodiment of the present invention.

FIG. 1A is a front view of a wetsuit 10 with a lumbar support features according to an embodiment of the present invention. The wetsuit 10 can comprise foam rubber. In certain embodiments, the foam rubber is Neoprene. In certain embodiments, the wetsuit 10 comprises one or more panels of foam rubber or another wetsuit material.

In certain embodiments, the panels comprise at least an inner layer of laminated nylon or other material. The laminated inner layer can provide strength and added water-resistance. Some of the panels can be more or less pliable than others. In particular, certain regions in the upper body portion of the wetsuit 10 can be significantly more stretchy and flexible than a majority of the trunk portion of the wetsuit 10. This construction provides for more heat insulation in the trunk and leg areas while providing less restriction for the movement of the arms. Certain embodiments of the wetsuit 10 are constructed entirely of foam rubber sandwiched between two laminates of nylon or other material, inside and outside. This type of wetsuit material is very durable, and has a high heat insulation capacity. Certain embodiments of the wetsuit 10 are composed of panels of one, two, or three different thicknesses which usually range from one millimeter to eight millimeters. In certain embodiments, one or more panels have a variable thickness.

The wetsuit 10 illustrated in FIG. 1A comprises a lumbar portion 20 and an upper torso portion 40. In certain embodiments, the lumbar portion 20 can be embedded within the wetsuit. The lumbar portion 20 can be interposed between layers of foam rubber or other wetsuit materials. The upper torso portion 40 extends from the neck of the wetsuit 10 down to the lower back area and the lower half of the ribcage on a front side. The upper torso portion 40 may cover at least a portion of the arms of the wearer of the wetsuit 10. The lumbar portion 20 covers at least a portion of the lower back or lumbar area. The lumbar portion 20 generally spans from somewhere at the lower half of the wearer's ribcage to the waist or a bit below the waist. The lumbar portion 20 can extend around the entire circumference of the wetsuit, i.e. anterior to posterior.

In certain embodiments, the wetsuit 10 comprises a leg portion 30. The leg portion 30 of the wetsuit 10 can cover some portion of the area approximately from the wearer's waist to their ankles.

Figure 1B:
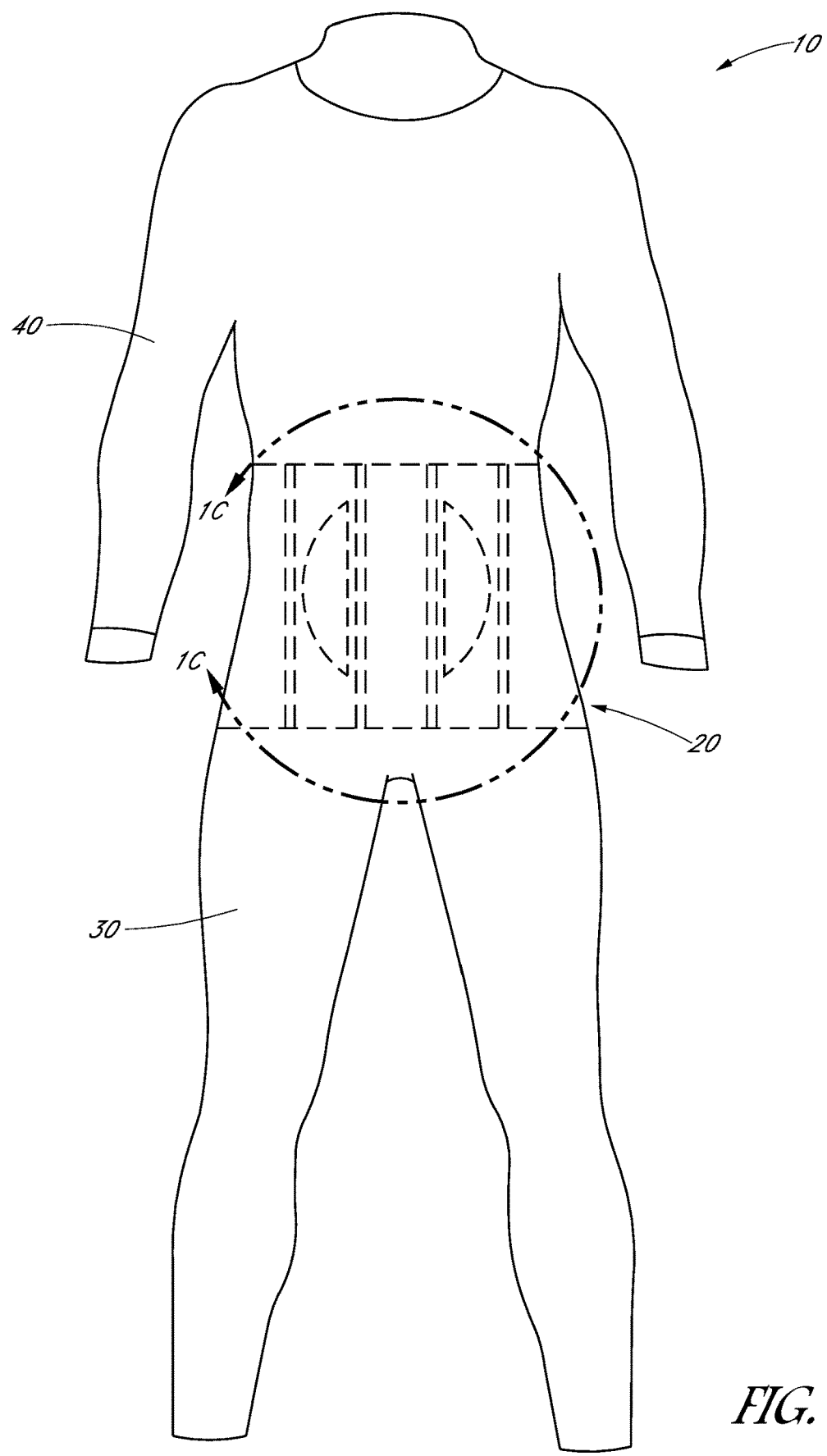
FIG. 1B is a back view of the wetsuit from FIG. 1A with inner components shown in dashed lines.
Figure 1C:
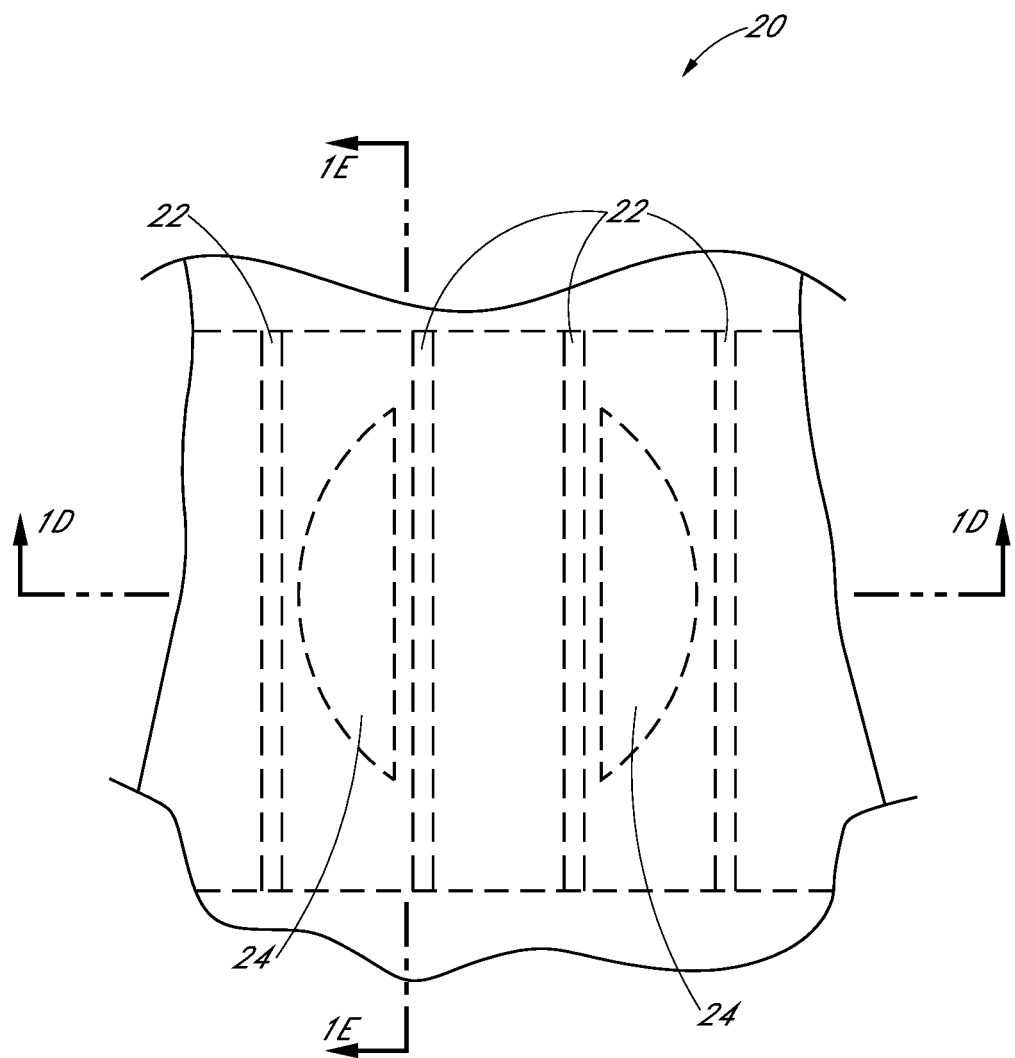
FIG. 1C is a zoomed-in, partial back view of the lumbar portion of FIG. 1B encircled by line 1C-1C.

In certain embodiments, the lumbar portion 20 can comprise one or more struts 22 as is illustrated in FIGS. 1B and 1C. In certain embodiments, the one or more struts 22 are disposed internally within the foam rubber or other wetsuit material. In certain embodiments, the lumbar portion 20 can comprise one or more pressure pads 24. In some embodiments, the one or more struts 22 and/or one or more pressure pads 24 can be integrated into the wetsuit 10. In certain embodiments where integrated into the wetsuit 10, the one or more struts 22 and/or one or more pressure pads 24 can be embedded in the wetsuit 10. In certain embodiments, the one or more struts 22 and/or one or more pressure pads 24 can provide support and rigidity.

A person of skill in the art will recognize that the design of the wetsuit 10 can vary in many ways from the design shown in FIG. 1A. For example, FIG. 1A depicts a standard full-length, chest-zip wetsuit 10. In some embodiments of the wetsuit 10, the upper portion 40 may terminate around the middle of the bicep area and the leg portion 30 may terminate around the middle of the quadriceps area, a design also known as a "spring suit." In certain embodiments, the arms of the upper portion 40 can be cut-off like a tank top. In certain embodiments, the wetsuit 10 may not include the lower portion 30 or the lower portion 30 may terminate at the top of the legs.

In certain embodiments, the wetsuit 10 comprises one or more fasteners 11 configured to facilitate a person to put on the wetsuit 10. In some embodiments, the fastener 11 can be arranged in a different manner. For example, the upper piece of the wetsuit 10 that contains the neck hole can be arranged such that it is only connected in the back when unfastened and it must be pulled over the back of the person's head when used. In certain embodiments, the fastener 11 can be a zipper disposed on the back of the wetsuit 10 such that when unzipped, a person can step into the back of the wetsuit 10. A chest-zip style can be preferable in some embodiments because it does not interfere with the lumbar portion 20 and can be better at keeping water out of the wetsuit 10. In certain embodiments, the back-zip style can be preferable so that the wetsuit 10 is easier to put on. In back-zip embodiments, the zipper can terminate before it reaches the lumbar portion 20. In other designs, additional types of fasteners 11 can be preferable.

In certain embodiments, the upper torso portion 40 has the one or more fasteners 11. In certain embodiments, the one or more fasteners 11 are disposed on the upper chest area of the wetsuit 10. Each fastener 11 can hold two pieces of the wetsuit 10 together and allow them to be separated when the fastener 11 is unfastened. The fastener 11 can allow a person to more easily enter the wetsuit 10 by allowing the wetsuit 10 to open up when the fastener 11 is unfastened. The upper piece of the wetsuit 10 connected to the fastener 11 can be pulled to the side when the fastener 11 is unfastened which provides an opening larger than the neck hole through which a person can enter the wetsuit 10. Additionally, the upper piece of the wetsuit 10 that is connected to the fastener 11 can contain a neck portion which slides over a person's head after they have entered the wetsuit 10. The fastener 11 is then fastened which can secures the wetsuit 10 on the person's body. In this non-limiting embodiment, the fastener 11 is a zipper that runs horizontally across the upper chest.

FIG. 1B is a back view of the wetsuit 10 from FIG. 1A with inner components shown in dashed lines. FIG. 1C is a zoomed-in, partial back view of the lumbar portion 20 of FIG. 1B encircled by line 1C-1C. The lumbar portion 20 can comprise the one or more struts 22. In certain embodiments, the one or more struts 22 can be arranged vertically. The one or more struts 22 can run from the top of the lumbar portion 20 to the bottom. In some embodiments, the one or more struts 22 can also be arranged to span only a portion of the lumbar portion 20.

The one or more struts 22 can extend at least partially across the lumbosacral and/or paravertebral lumbar area. The one or more struts 22 can apply pressure on the muscles in the lumbosacral and/or paravertebral lumbar area. This pressure may alleviate strain on muscles in the lumbosacral and/or paravertebral lumbar area. A person of skill in the art will recognize that the one or more struts 22 can be made from many different substantially rigid materials including, but not limited to, high-density polyethylene, other similar materials, other plastics, metals, metal alloys, polymers, or some combination thereof.

The one or more pressure pads 24 can run from the top of the lumbar portion 20 to the bottom. In some embodiments, the one or more pressure pads 24 can also be arranged to span only a portion of the lumbar portion 20. The one or more pressure pads 24 can extend at least partially across the lumbosacral and/or paravertebral lumbar area. In certain embodiments, the one or more pressure pads 24 can apply pressure to the muscles in the lumbosacral and/or paravertebral lumbar area. In certain embodiments, the one or more pressure pads 24 are located in line with the one or more struts 22. The one or more pressure pads 24 can be disposed between the one or more struts 22. In certain embodiments, the one or more pressure pads 24 are spaced apart along a length of the lumbar portion 20.

In certain embodiments, the one or more pressure pads 24 can be disposed on the inner side of the one or more struts 22. In certain embodiments, the one or more pressure pads 24 can be disposed on the outer side of the one or more struts 22. In certain embodiments, the one or more pressure pads 24 can be co-linear with the one or more struts 22.

In certain embodiments, the one or more pressure pads 24 can be arranged vertically. In certain embodiments, the one or more pressure pads 24 can be arranged horizontally. In certain embodiments, the one or more pressure pads 24 can be arranged at some angle in between vertical and horizontal. In certain embodiments, the one or more pressure pads 24 can extend along the entire vertical, horizontal, or angled length of the lumbar portion 20.

The one or more pressure pads 24 can be made from a variety of different materials including but not limited to foams, rubbers, latexes, or some combination thereof. In some embodiments, the one or more pressure pads 24 can be or can include pockets filled with air. The pockets filled with air can allow for the amount of air inside the pockets to be adjustable. In embodiments where the one or more pressure pads 24 are or include pockets filled with air, the one or more pressure pads 24 can provide extra buoyancy for the person wearing the wetsuit. In certain embodiments, the one or more pressure pads 24 can be disposed in the curve of the small of the back.

In certain embodiments, the lumbar portion 20 can be made from a different thickness of wetsuit material than another portion of the wetsuit 10. In certain embodiments, the lumbar portion 20 can be made of a different material than another portion of the wetsuit 10. The lumbar portion 20 can be made of a material that provides more flexibility. In certain embodiments, the lumbar portion 20 can be made of a material with greater rigidity to enhance the supportive function. In some embodiments, the lumbar portion 20 can be made from a different material to allow for a person to select and change the one or more struts 22 or one or more pressure pads 24. In certain embodiments, at least some portion of the lumbar portion 20 can be made from the same panel as the torso portion 40 or the leg portion 30.

Figure 1D:
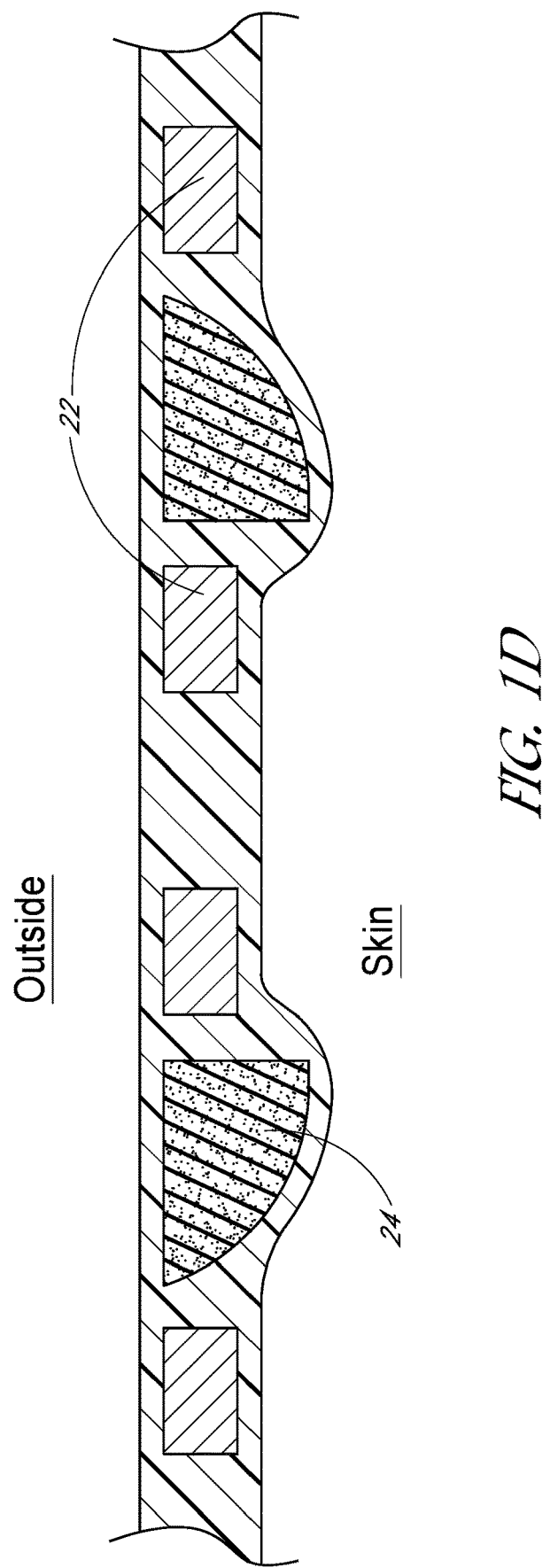
FIG. 1D is a horizontal cross-sectional view through the lumbar portion of FIG. 1C taken along line 1D-1D.
Figure 1E:
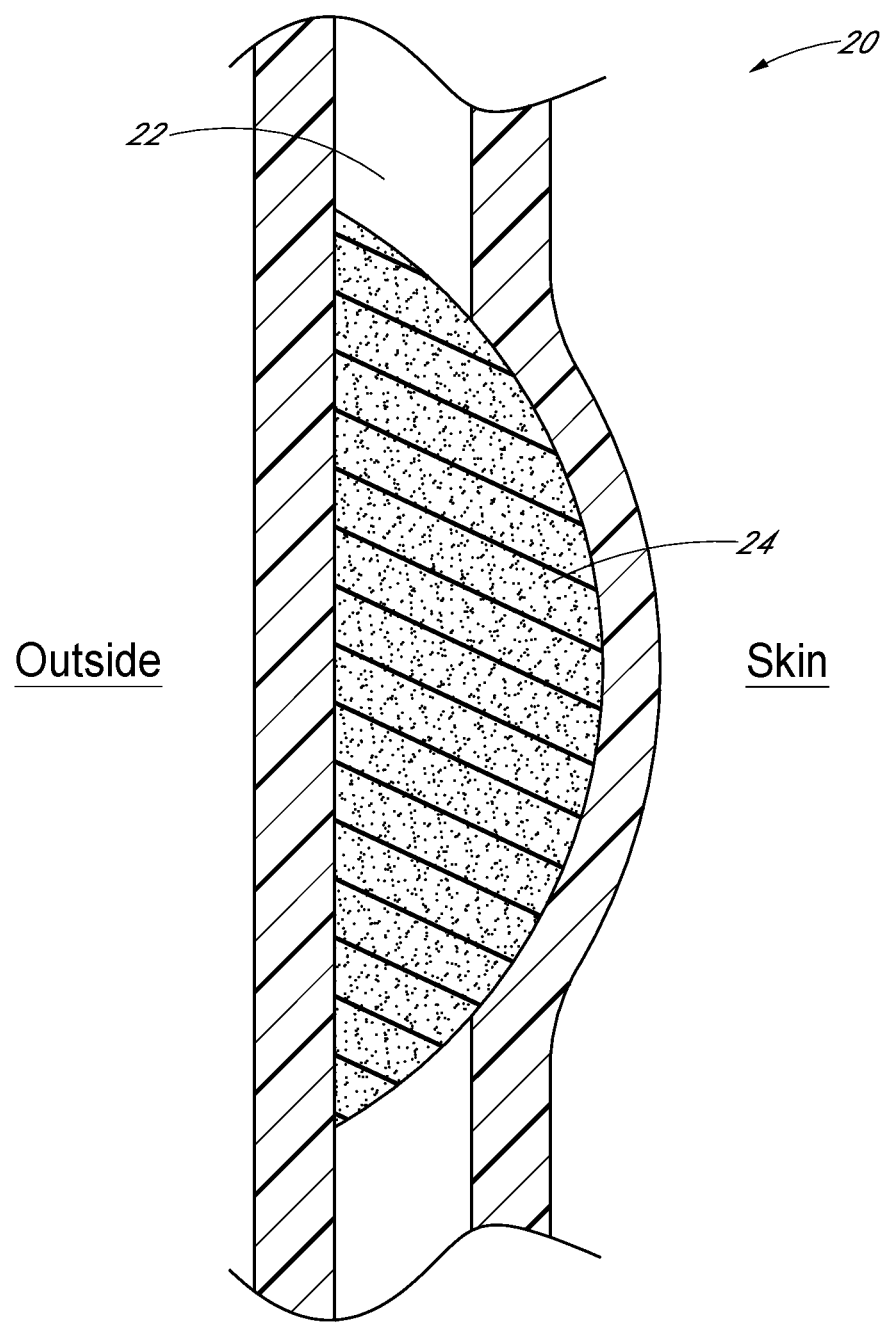
FIG. 1E shows a vertical cross-sectional view through the lumbar portion of FIG. 1C taken along line 1E-1E.

FIGS. 1D and 1E are cross-sectional views through an embodiment of the wetsuit 10 that includes the one or more struts 22 and the one or more pressure pads 24. FIG. 1D shows a horizontal cross-sectional view through the lumbar portion 20 of FIG. 1C taken along line 1D-1D. In FIG. 1D, the one or more struts 22 are disposed internally within the foam rubber or other wetsuit material. In certain embodiments, the one or more struts 22 can be disposed between a first layer of wetsuit material and a second layer of wetsuit material. In certain embodiments, the one or more struts 22 can be arranged closer to the inside or outside of the wetsuit 10. In certain embodiments, the one or more struts 22 can be disposed on the inside or outside of the foam rubber or other wetsuit material. In embodiments where the one or more struts 22 are arranged on the inside or outside of the foam rubber or other wetsuit material, the one or more struts 22 and/or one or more pressure pads 24 can be removably integrated into the wetsuit 10. In certain embodiments, a band of wetsuit material connects to the one or more struts 22 and/or the one or more pressure pads 24. In certain embodiments, a band or large strip of wetsuit material can enable the one or more struts 22 and/or the one or more pressure pads 24 to be removed and/or interchanged. The one or more struts 22 and/or the one or more pressure pads 24 can also be arranged in between two separate layers of foam rubber or another wetsuit material.

FIG. 1E shows a vertical cross-sectional view through the lumbar portion 20 of FIG. 1C taken along line 1E-1E. This view shows one strut of the one or more struts 22 disposed behind one pressure pad 24 of the one or more pressure pads 24. In certain embodiments, the one or more struts 22 and/or one or more pressure pads 24 can be embedded within the wetsuit 10. In certain embodiments, tension or pressure can be applied to the lumbosacral and/or paravertebral lumbar by putting on the wetsuit 10. In certain embodiments, the one or more struts 22 and/or one or more pressure pads 24 can apply pressure as a result of the tension of the wetsuit material. Additionally, in some embodiments, there can be no struts 22. In some embodiments, there can be no pressure pads 24. In some embodiments, the one or more struts 22 can be replaced by one or more pressure pads 24.

Figure 2A:
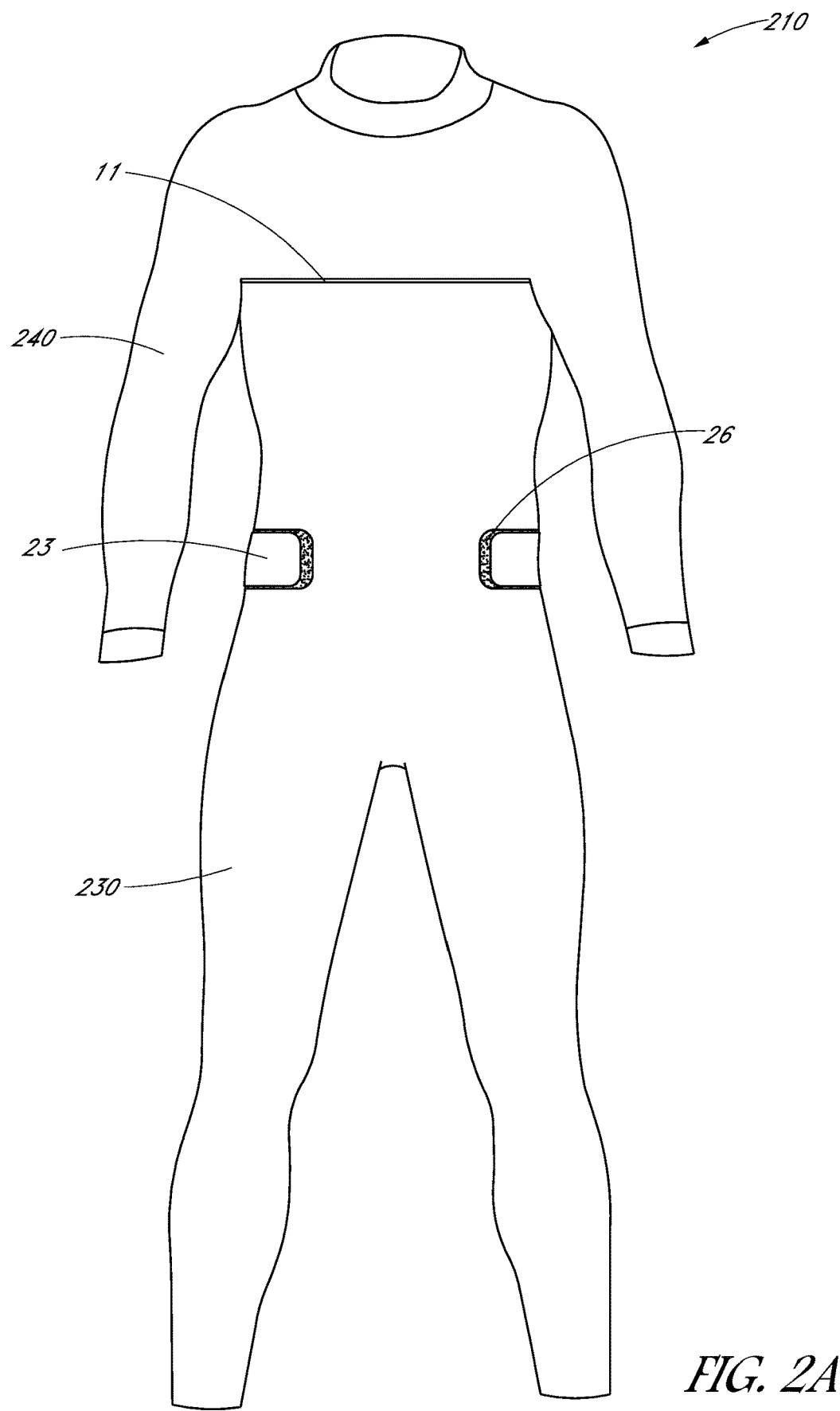
FIG. 2A is a front view of another embodiment of a wetsuit having one or more tensioning mechanisms in the form of an external strap around a lumbar portion.
Figure 2B:
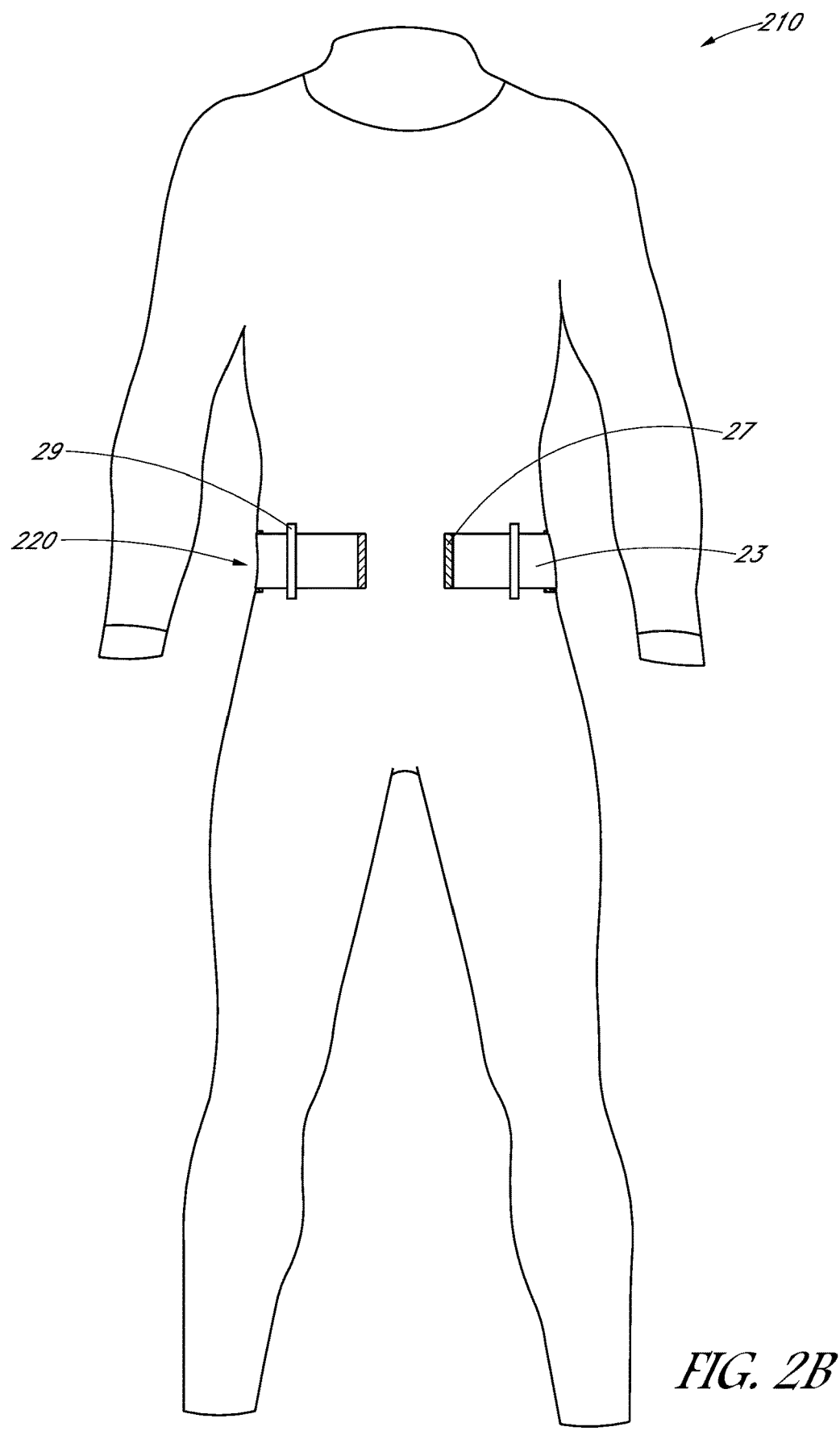
FIG. 2B is a back view of the wetsuit from FIG. 2A showing the external strap around the lumbar portion.
Figure 2C:
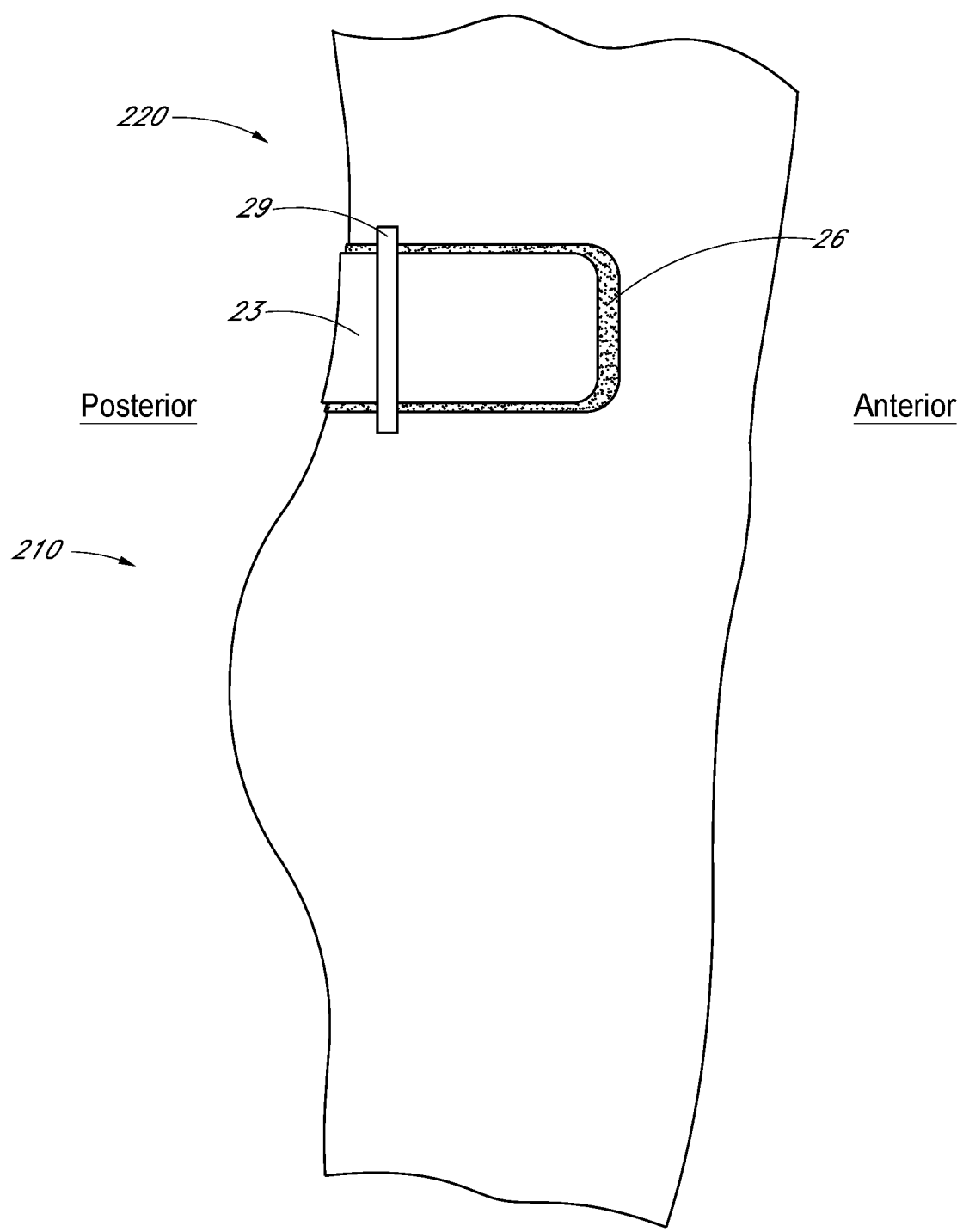
FIG. 2C is a right-side view of the wetsuit from FIG. 2A showing the external strap around the lumbar portion.

FIGS. 2A-2C illustrate an embodiment of a wetsuit 210 having one or more internal or external tensioning mechanisms. In certain embodiments, the tensioning mechanism applies or transfers tension to the wetsuit 210. This tensioning mechanism can be composed of elastic straps, wires, gearing, pulleys, ratchets, and/or various other types of mechanical or electrical tensioners. In certain embodiments, the tensioning mechanism is connected to a dial on the outside of the wetsuit 210. The dial could be used to increase and decrease the tension. In certain embodiments, the tensioning mechanism is one or more straps 23. The one or more straps 23 can be tensioned by their own elasticity. The one or more straps 23 can be tensioned by being secured in a taught position.

FIG. 2A shows a front view of the wetsuit 210. In the illustrated embodiment, the tensioning mechanism comprises the one or more straps 23 disposed in the lumbar portion 220. In certain embodiments, each of the one or more straps 23 can comprise a central portion and one or more end portions. In certain embodiments, the one or more straps 23 can be completely disposed outside the wetsuit 210. In certain embodiments, the one or more straps 23 wrap around more than the full circumference of the wetsuit 210. In certain embodiments, the one or more straps 23 comprise an elastic material. In certain embodiments, the one or more straps 23 can comprise wetsuit material. In certain embodiments, the one or more straps 23 can comprise one or more bands or straps of wetsuit material. In certain embodiments, the one or more straps 23 can comprise a substantially inelastic material.

The one or more straps 23 can comprise one or more securement mechanisms 26. In certain embodiments, the one or more securement mechanisms 26 are integrated with the one or more straps 23. In certain embodiments, the one or more securement mechanisms 26 are separate from the one or more straps 23. The one or more securement mechanisms 26 can substantially prevent the one or more straps 23 from moving once engaged. In some embodiments, the one or more securement mechanisms 26 can prevent the lumbar portion 220 from losing tension.

In certain embodiments, each of the one or more straps 23 can comprise a central portion and one or more end portions (as seen in FIG. 2B). In certain embodiments, the one or more straps 23 comprise one or more right straps disposed on the right-hand side of the wetsuit 210 and one or more left straps disposed on the left-hand side of the wetsuit 210. In certain embodiments with right and left straps, the one or more straps 23 can each comprise a strap anchor portion 27, a central portion, and a securement mechanism 26. The one or more securement mechanisms 26 can be used to attach the one or more straps 23 to the outer surface of the lumbar portion 220 of the wetsuit 210. In certain embodiments, the one or more securement portions 26 are wings formed at the end of the one or more straps 23. Attaching the one or more straps 23 to the outer surface of the lumbar portion 220 of the wetsuit 210 can enable the one or more straps 23 to maintain tension on the lumbar portion 220. The one or more securement mechanisms 26 can substantially prevent the one or more straps 23 from moving once engaged. In certain embodiments, the outer surface of the lumbar portion 220 can have one or more portions that engage, interact, or mate with the one or more securement mechanisms 26. In certain embodiments where the one or more securement mechanisms 26 comprise Velcro, the one or more securement mechanisms 26 can comprise Velcro hooks. In certain embodiments where the one or more securement mechanisms 26 comprise the Velcro hooks, the one or more portions on the lumbar portion 220 can comprise the Velcro loops.

The wearer can apply tension to the one or more straps 23 by changing the position of one or more end portions of the one or more straps 23. In some embodiments, the one or more straps 23 wrap around the entire circumference of the wetsuit 210. In certain embodiments, the one or more straps 23 wrap part of the way around the circumference of the wetsuit 210. One of skill in the art will recognize that the one or more securement mechanism 26 can be a variety of different mechanisms used to prevent the one or more straps 23 from moving substantially which can include, but are not limited to Velcro, buttons, magnets, friction locks, or some other mechanical locking device.

FIG. 2B shows a back view of a wetsuit 210 having an external strap around the lumbar portion 220. In certain embodiments, the one or more straps 23 can comprise one or more strap anchor portions 27. In certain embodiments, the one or more strap anchor portions 27 can be disposed on the opposite end of the one or more straps 23 as the one or more securement mechanisms 26. In certain embodiments, the one or more strap anchor portions 27 can be permanently attached to the outer surface of the wetsuit 210. In certain embodiments, the one or more strap anchor portions 27 can be integral with the wetsuit 210 so that the one or more straps 23 are formed with the wetsuit 210. The one or more strap anchor portions 27 can be attached to the wetsuit 210 in ways that include but are not limited to using glue, stitching, liquid seams, bonding, other ways of chemical or mechanical joining or some combination thereof. In certain embodiments, the one or more strap anchor portions 27 can be embedded in the wetsuit material. In certain embodiments, the one or more strap anchor portions 27 can be removably connected to an outer surface of the wetsuit 210. One of skill in the art will recognize that the one or more strap anchor portions 27 can comprise a variety of different mechanisms which can include, but are not limited to Velcro, buttons, magnets, friction locks, or some other mechanical locking device. In this embodiment, the strap 23 runs from posterior to anterior. In certain embodiments, the one or more straps 23 can run from anterior to posterior. In certain embodiments, the one or more strap anchor portions 27 can be disposed on the anterior or side portions of the wetsuit 210 and the one or more securement mechanisms 26 can be disposed on the posterior portion of the wetsuit 210. Additionally, the wetsuit 210 can comprise one or more straps 23 running from posterior to anterior and one or more straps 23 running from anterior to posterior.

In some embodiments, the wetsuit 210 can comprise one or more belt loops 29. The one or more belt loops 29 can retain the one or more straps 23. By retaining the one or more straps 23, the one or more belt loops 29 can prevent at least a portion of the one or more straps 23 from dangling from the one or more strap anchor portions 27. In embodiments where there is a single strap 23, the one or more belt loops 29 can prevent the single strap 23 from falling off of the wetsuit 210 when the one or more securement mechanisms 26 are not securing the one or more straps 23 to the wetsuit 210.

FIG. 2C shows a partial right-side view of the wetsuit 210 from FIG. 2A. In some embodiments, the right-side view of the wetsuit 210 is substantially symmetrical to the left-side view of the wetsuit 210. In some embodiments, the right-side view of the wetsuit 210 is not substantially symmetrical to the left-side view of the wetsuit 210.

Figure 3A:
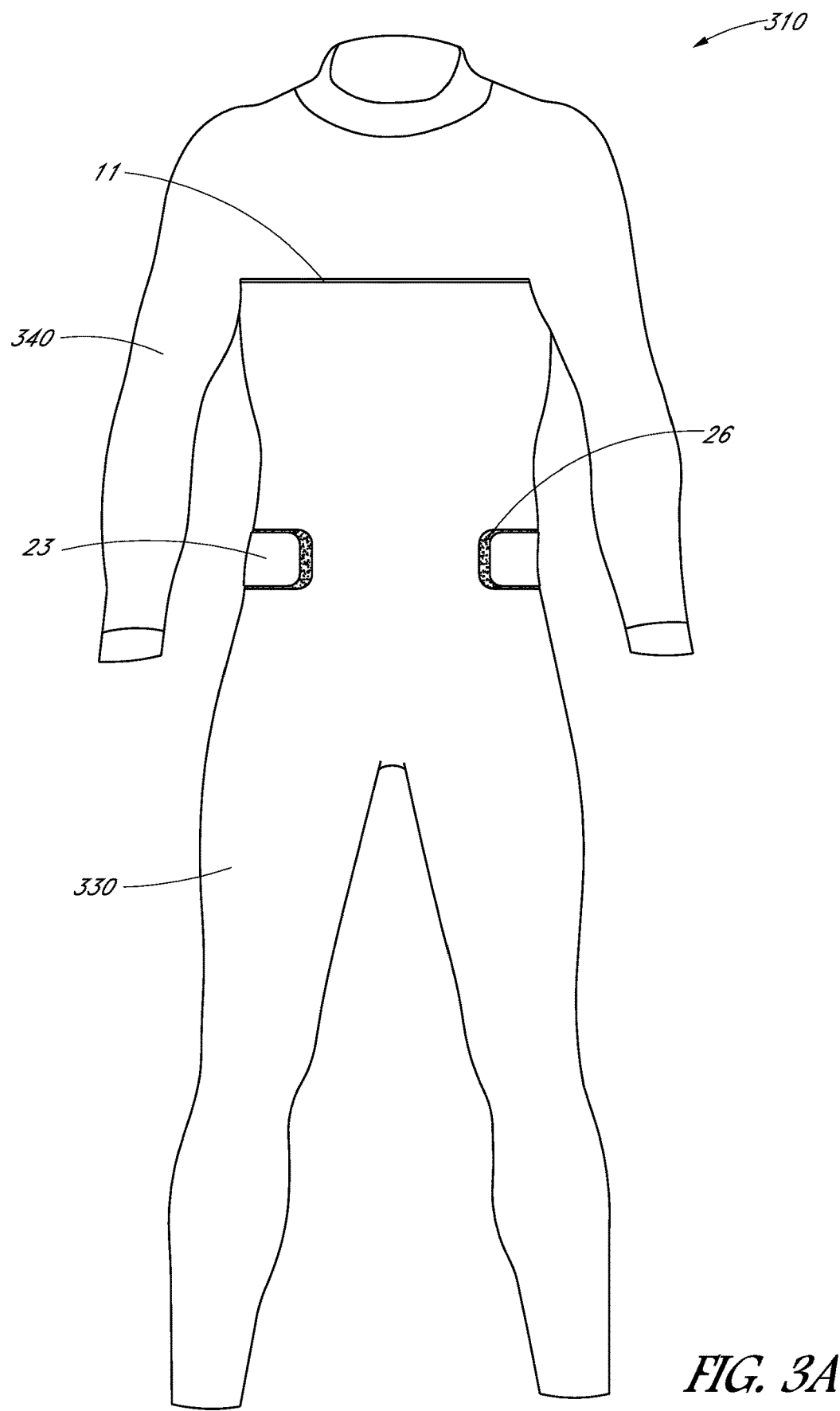
FIG. 3A is a front view of another embodiment of a wetsuit having a partially-internal strap around a lumbar portion.
Figure 3B:
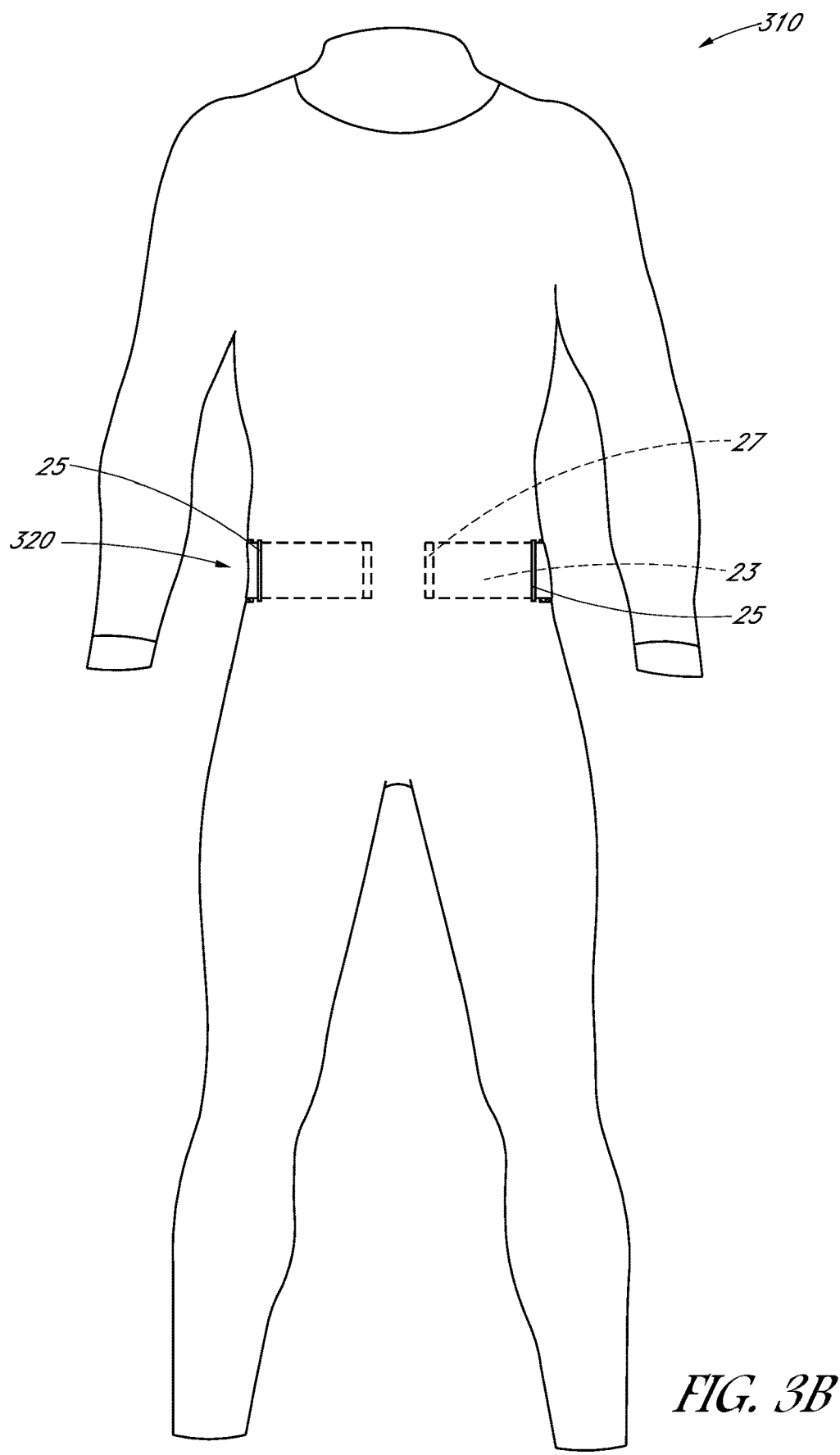
FIG. 3B is a back view of the wetsuit from FIG. 3A showing the partially-internal strap around the lumbar portion.
Figure 3C:
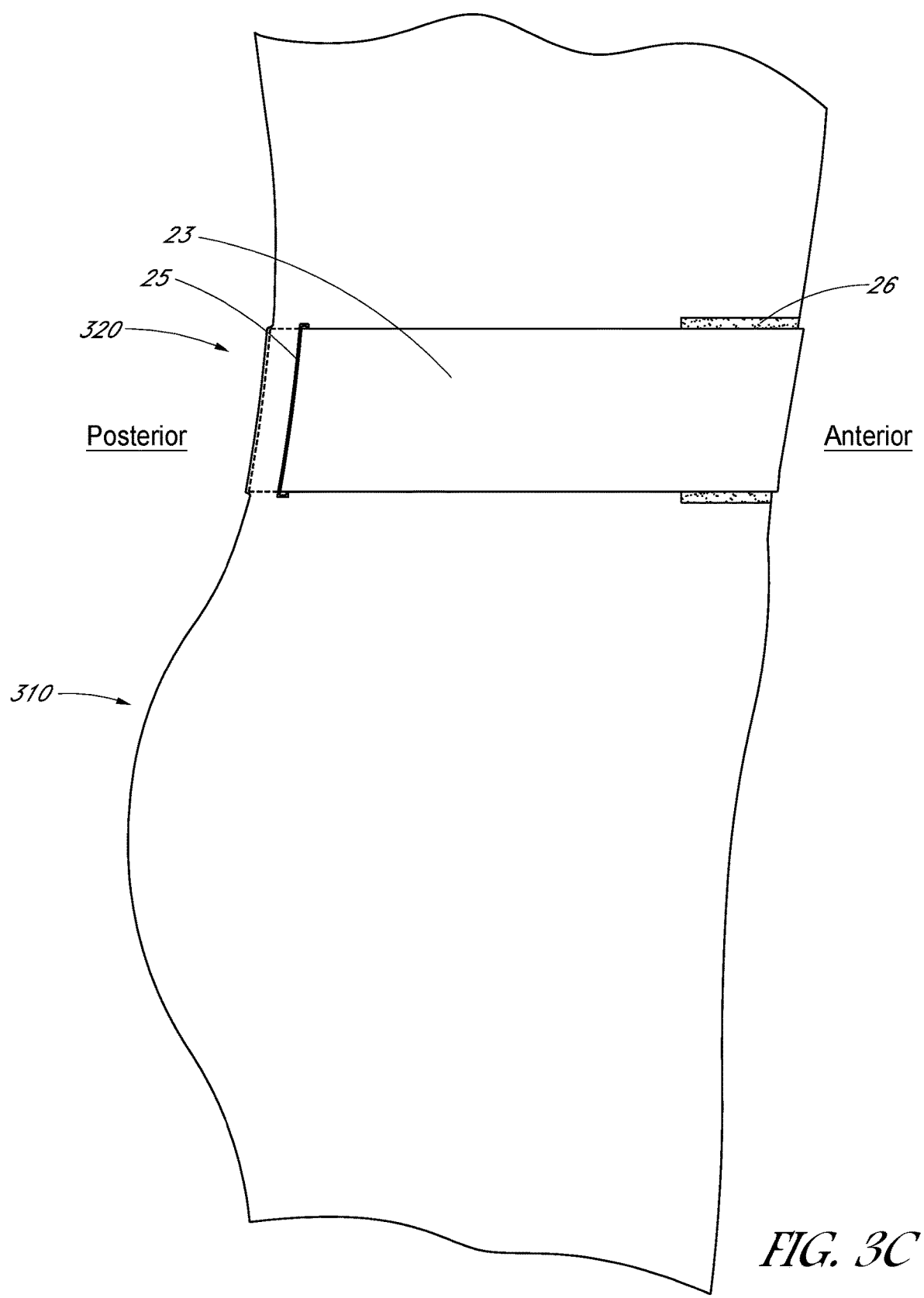
FIG. 3C is a right-side view of the wetsuit from FIG. 3A showing the partially-internal strap around the lumbar portion.

FIGS. 3A to 3C illustrate an embodiment of a wetsuit 310 having one or more internal or external tensioning mechanisms. In the illustrated embodiment, the tensioning mechanism is one or more straps 23. The one or more straps 23 include an internal portion within the wetsuit 210. For example, the internal portion of the strap 23 is disposed in a lumbar portion 320 of the wetsuit 310. Inner components are shown in dashed lines in FIGS. 3B and 3C. In some embodiments, the one or more straps 23 allow the wearer to selectively change a level of the support provided to the lumbosacral region of the wearer by the lumbar portion 320. In certain embodiments, each of the one or more straps 23 can comprise a central portion and one or more end portions. In certain embodiments, the one or more end portions pass through at least one layer of the wetsuit material.

FIG. 3A is a front view of the wetsuit 310 having a partially-internal strap 23 around the lumbar portion 320. This view shows an embodiment where the one or more straps 23 have an external portion located outside of the wetsuit 310. In certain embodiments, one or more external portions of the one or more straps 23 are secured by one or more securement mechanisms 26. The one or more securement mechanisms 26 can secure one or more external portions of the one or more straps 23 to the wetsuit 310. In certain embodiments, the one or more securement mechanisms 26 are integrated with the one or more straps 23. In certain embodiments, the one or more securement mechanisms 26 are separate from the one or more straps 23. The one or more securement mechanisms 26 can substantially prevent the one or more straps 23 from moving once engaged. In some embodiments, the one or more securement mechanisms 26 can prevent the lumbar portion 320 from losing tension.

FIG. 3B shows a back view of the wetsuit 310 from FIG. 3A. Inner components are shown in dashed lines. FIG. 3C shows a partial right-side view of the wetsuit 310 and the strap 23 extending around the lumbar portion 320.

In certain embodiments, one or more openings 25 are provided in the wetsuit 310. The one or more openings 25 can be located on the lumbar portion 320. In certain embodiments, the one or more openings 25 are located on an upper portion 340 of the wetsuit 310. In certain embodiments, the one or more straps 23 pass through the one or more openings 25. The one or more securement mechanisms 26 can be disposed in or near to the one or more openings 25. For example, in certain embodiments the one or more openings 25 can be plastic rings or rectangles through which the one or more straps 23 pass. In certain embodiments, the one or more securement mechanisms 26 can clamp down on the one or more straps 23 to prevent movement. In certain embodiments, the one or more securement mechanisms 26 can prevent movement of the one or more straps 23 by providing friction between the one or more straps 23 and the one or more securement mechanisms 26. In some embodiments, the one or more openings 25 can have one or more gaskets or seals. The one or more gaskets or seals can allow the one or more straps 23 to pass through one or more openings 25 while significantly preventing additional water from flowing into the wetsuit 310. In certain embodiments, the central portions of each strap 23 can terminate in the lumbar portion 320 so that the central portion of one strap 23 does not connect to the central portion of another strap 23 as shown in FIG. 3B.

In certain embodiments, the one or more straps 23 can comprise one or more strap anchor portions 27. In certain embodiments, the one or more strap anchor portions 27 can be disposed on the opposite end of the one or more straps 23 from the one or more securement mechanisms 26. In certain embodiments, the one or more strap anchor portions 27 can be integral with the wetsuit 310 so that the one or more straps 23 are formed with the wetsuit 310. The one or more strap anchor portions 27 can be attached to the wetsuit 310 in ways that include but are not limited to using glue, stitching, liquid seams, bonding, other ways of chemical or mechanical joining or some combination thereof. In certain embodiments, the one or more strap anchor portions 27 can be embedded in the wetsuit material. In certain embodiments, the central portion of each strap 23 is anchored in a first layer of wetsuit material. In certain embodiments, the central portion of each strap 23 is anchored in a second layer of wetsuit material. In certain embodiments, the central portion of each strap 23 is anchored between two layers of wetsuit material. One of skill in the art will recognize that the one or more strap anchor portions 27 can comprise a variety of different mechanisms which can include, but are not limited to Velcro, buttons, magnets, friction locks, or some other mechanical locking device. In this embodiment, the strap 23 runs from posterior to anterior. In certain embodiments, the one or more straps 23 can run from anterior to posterior. In certain embodiments, the one or more strap anchor portions 27 can be disposed on the anterior or side portions of the wetsuit 310 and the one or more securement mechanisms 26 can be disposed on the posterior portion of the wetsuit 310. Additionally, the wetsuit 310 can comprise one or more straps 23 running from posterior to anterior and one or more straps 23 running from anterior to posterior.

FIG. 3C shows a partial right-side view of the wetsuit 310 having a partially-internal strap around the lumbar portion 320. In some embodiments, the right-side view of the wetsuit 310 is substantially symmetrical to the left-side view of the wetsuit 310. In some embodiments, the right-side view of the wetsuit 310 is not substantially symmetrical to the left-side view of the wetsuit 310.

Figures 4A, 4B:
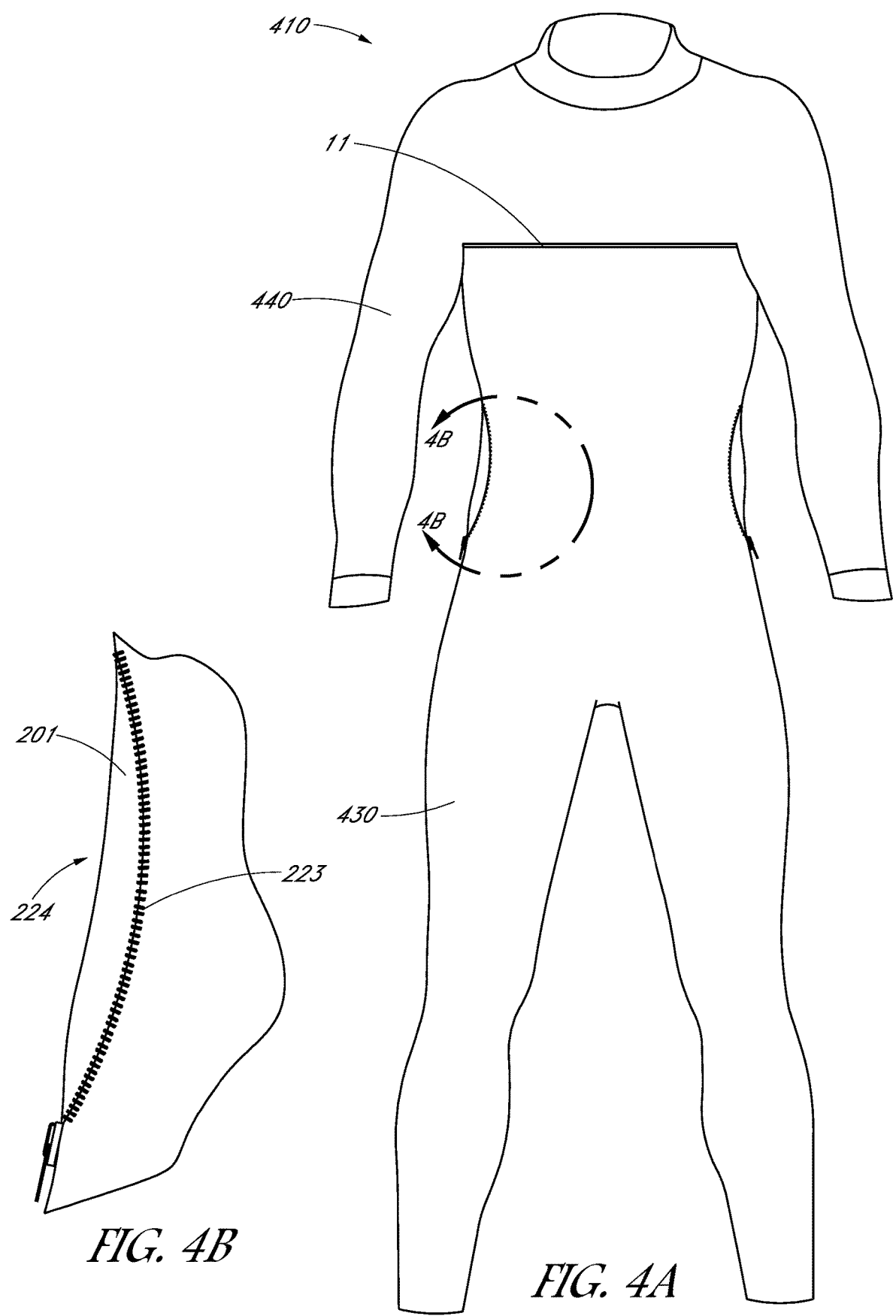
FIG. 4A is a front view of another embodiment of a wetsuit with a lumbar portion that comprises tensioning fasteners.
FIG. 4B a close-up view of a portion of the wetsuit in FIG. 4A indicated by circle 4B-4B.

FIGS. 4A-4E illustrate an embodiment of a wetsuit 410 with a lumbar portion 420 that comprises one or more tensioning mechanisms in the form of one or more fasteners 223. FIG. 4A shows a front view of the wetsuit 410. FIG. 4B shows a close-up view of a portion of the wetsuit 410 in FIG. 4A marked by circle 4B-4B. In certain embodiments, the lumbar portion 420 can comprise one or more tensioning fasteners 223. In some embodiments, the one or more tensioning fasteners 223 can be disposed on the anterior half of the wetsuit 410. In some embodiments, the one or more tensioning fasteners 223 can be disposed on the left and/or right side of the wetsuit 410. The one or more tensioning fasteners 223 can act to tension the lumbar portion 420.

In certain embodiments, the lumbar portion 420 can comprise one or more slots 224. The one or more tensioning fasteners 223 can fasten together the one or more slots 224 in the wetsuit material. In some embodiments, the one or more slots 224 are vertical and are surrounded on the interior portion of the wetsuit 410 by one or more pockets 201. In certain embodiments, the one or more pockets 201 include barrier material that functions to prevent water from entering the wetsuit 410. The one or more pockets 201 can function to prevent water from entering the wetsuit 410 when the one or more tensioning fasteners 223 are unfastened or in an open position. In certain embodiments, a portion of the lumbar portion 420 can connect to the one or more pockets 201. In certain embodiments, a portion of the lumbar portion 420 can connect directly to the one or more tensioning fasteners 223. In certain embodiments, a portion of the lumbar portion 420 can connect directly to the barrier material. In certain embodiments, the one or more straps 23 can connect directly to the one or more tensioning fasteners 223. In certain embodiments, the one or more straps 23 can connect directly to the barrier material of the one or more pockets 201.

In certain embodiments, fastening the tensioning fasteners 223 increases the tension in the lumbar portion 420 of the wetsuit 410. In certain embodiments, the one or more pockets 201 are able to stretch out and increase the circumference of the wetsuit 410 when the tensioning fasteners 223 are unfastened. Conversely, the fastening of the tensioning fasteners 223 can cause the slack in the one or more pockets 201 to be taken up. The taking up of slack in the one or more pockets 201 can cause the circumference of the wetsuit 410 to decrease. This decrease can be restricted by the circumference of the person wearing the wetsuit 410. This restriction can cause the components of the lumbar portion 420 to stretch instead of decrease in circumference. This stretching can result in a tension force in the lumbar portion 420 pulling on the one or more tensioning fasteners 223 or the one or more pockets 201. Increasing the tension of the lumbar portion 420 may increase the level of support provided on the lumbosacral or paravertebral area.

Figure 4C:
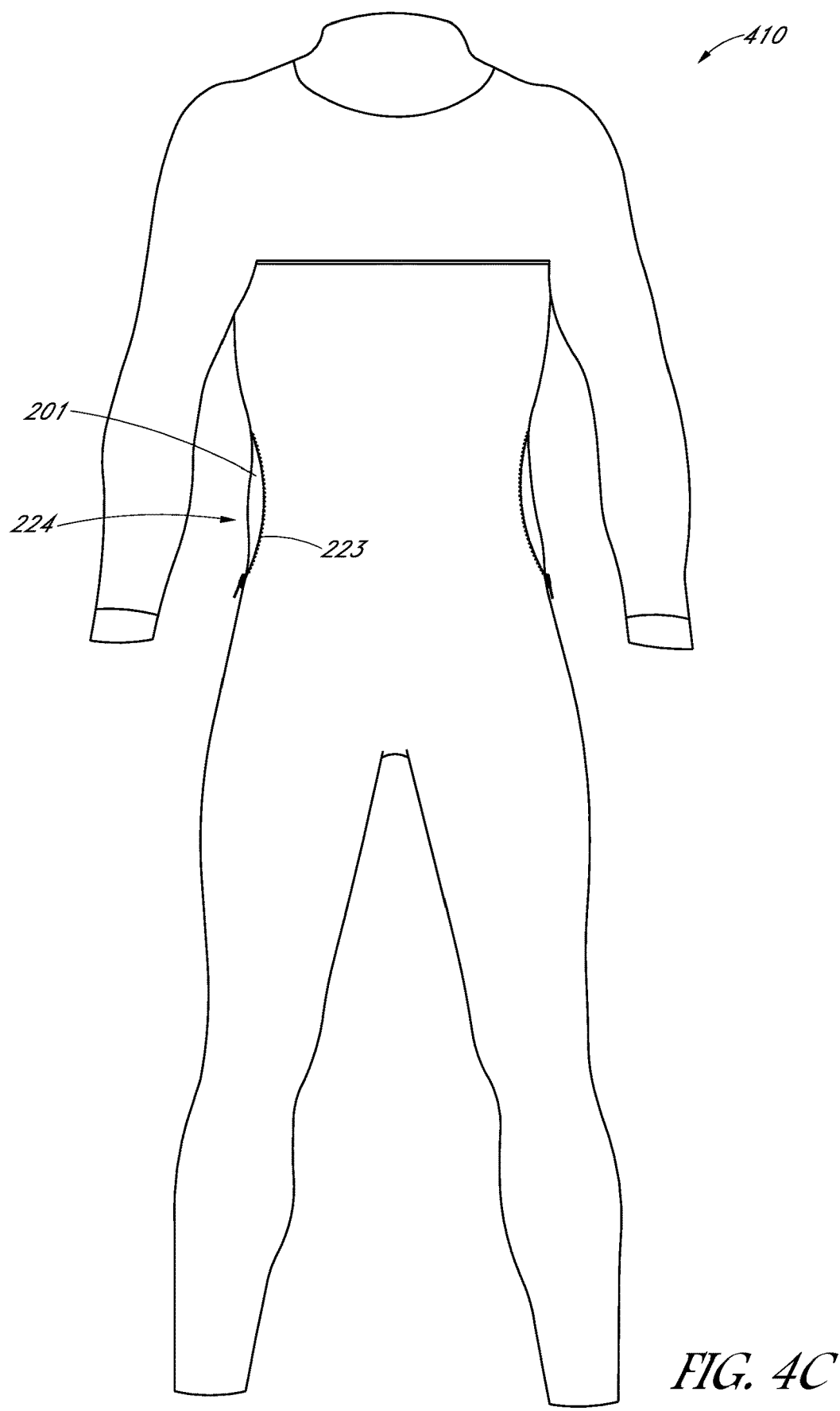
FIG. 4C is a rear view of the wetsuit in FIG. 4A showing the lumbar portion.
Figure 4D:
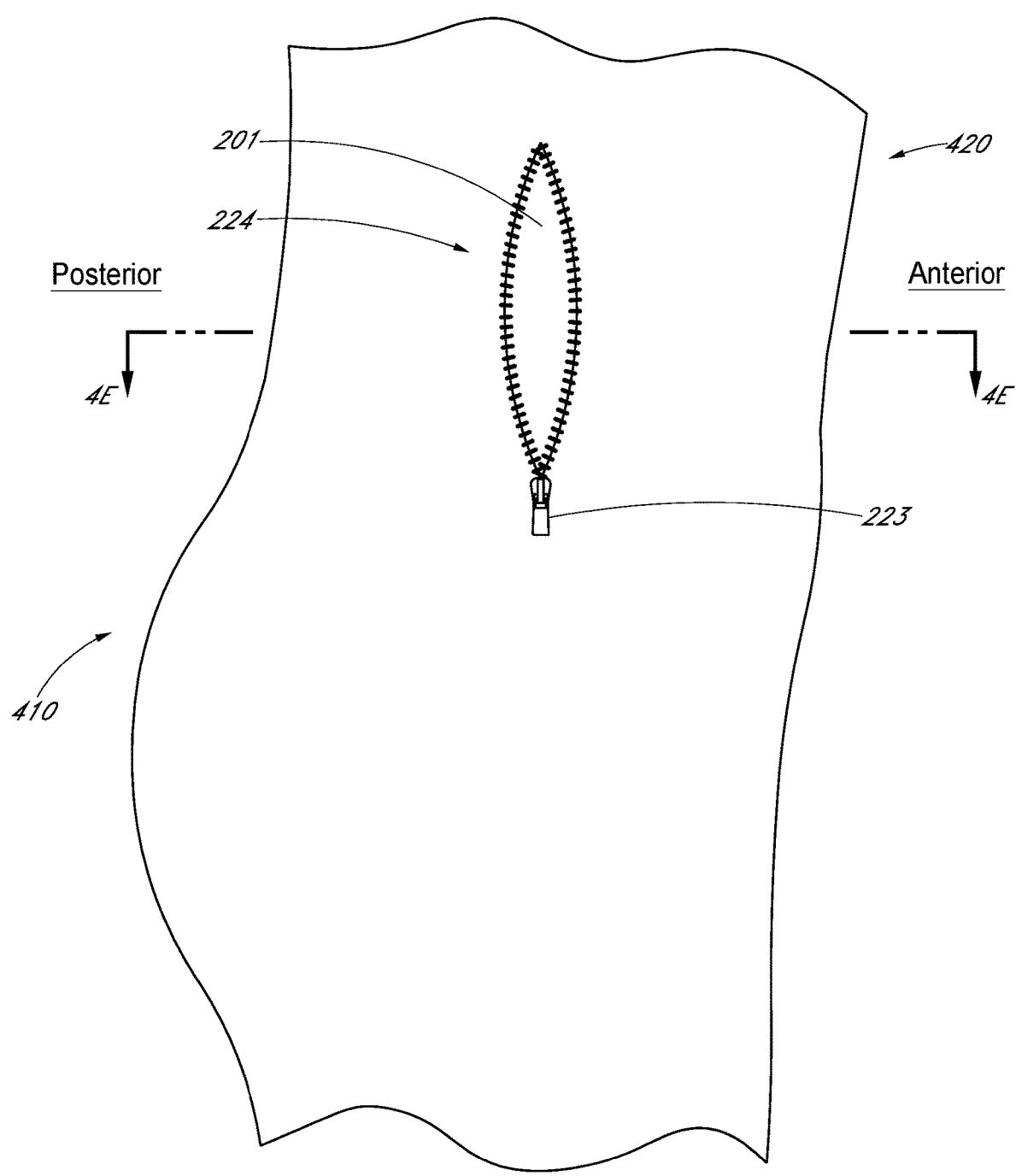
FIG. 4D is a right-side view of the wetsuit in FIG. 4A showing the tensioning fasteners in an open position.

FIG. 4C shows a rear view of the wetsuit 410 of FIG. 4A. FIG. 4D shows a partial right-side view of the wetsuit 410 of FIG. 4A. In certain embodiments, the one or more slots 224 are on the right-hand and left-hand sides of the lumbar portion 420. In some embodiments, the right-side view of the wetsuit 410 is substantially symmetrical to the left-side view of the wetsuit 410. In some embodiments, the right-side view of the wetsuit 410 is not substantially symmetrical to the left-side view of the wetsuit 410.

The one or more slots 224 can be used to cinch the lumbar portion 420. In embodiments with more than one slot 224, the amount of tension can be adjusted by incrementally fastening some of the tensioning fasteners 223. In certain embodiments, the barrier material can stretch from a first edge of the one or more slots 224 to a second edge. The barrier material can completely surround the interior portion of the opening created by the slot 224 when it is in an open or unfastened position. In certain embodiments, the fastener 223 can be capable of forming a barrier to water entering the wetsuit 410 when it is in a closed or fastened position. In the embodiment illustrated in FIGS. 4A-4E, the tensioning fasteners 223 are zippers. However, a person of skill in the art will appreciate that there are many other types of tensioning fasteners 223 that could be used. In certain embodiments, one tensioning fastener 223 can be used. In certain embodiments, a plurality of tensioning fasteners 223 can be used. Additionally, the lumbar portion 420 illustrated in FIGS. 4A-4E does not extend across the anterior portion of the wetsuit 410. In certain embodiments, the lumbar portion 420 will be disposed on both the posterior and anterior portions of the wetsuit 410.

FIG. 4E shows a horizontal cross-sectional view through the lumbar portion 420 taken along line 4E-4E of the wetsuit 410 in FIG. 4D. In certain embodiments, the lumbar portion 420 comprises a first layer 12a of wetsuit material. In certain embodiments, the lumbar portion 420 comprises a second layer 12b of wetsuit material. In certain embodiments, the first layer 12a of wetsuit material is the inner layer of the lumbar portion 420. In certain embodiments, the second layer 12b of wetsuit material is the outer layer of the lumbar portion 420. In certain embodiments, the one or more straps 23 will be disposed between the first layer 12a of wetsuit material and the second layer 12b of wetsuit material. In certain embodiments, the lumbar portion 420 will be disposed on the anterior and posterior portions of the wetsuit 410. In certain embodiments, the lumbar portion 420 will connect to one or more slots 224 on both the anterior and posterior sides of the one or more slots 224. By being disposed on the anterior and posterior portions of the wetsuit 410, the lumbar portion 420 can provide more tension than if it were only on the posterior because the lumbar portion 420 could provide a more rigid anterior portion that does not deform as easily as other wetsuit material. In certain embodiments, the lumbar portion 420 will encircle the circumference of the wetsuit 410 from anterior to posterior. In certain embodiments, the lumbar portion 420 may only be broken up by vertical slots when viewing the wetsuit 410 from the view of FIG. 4E.

Figure 5A:
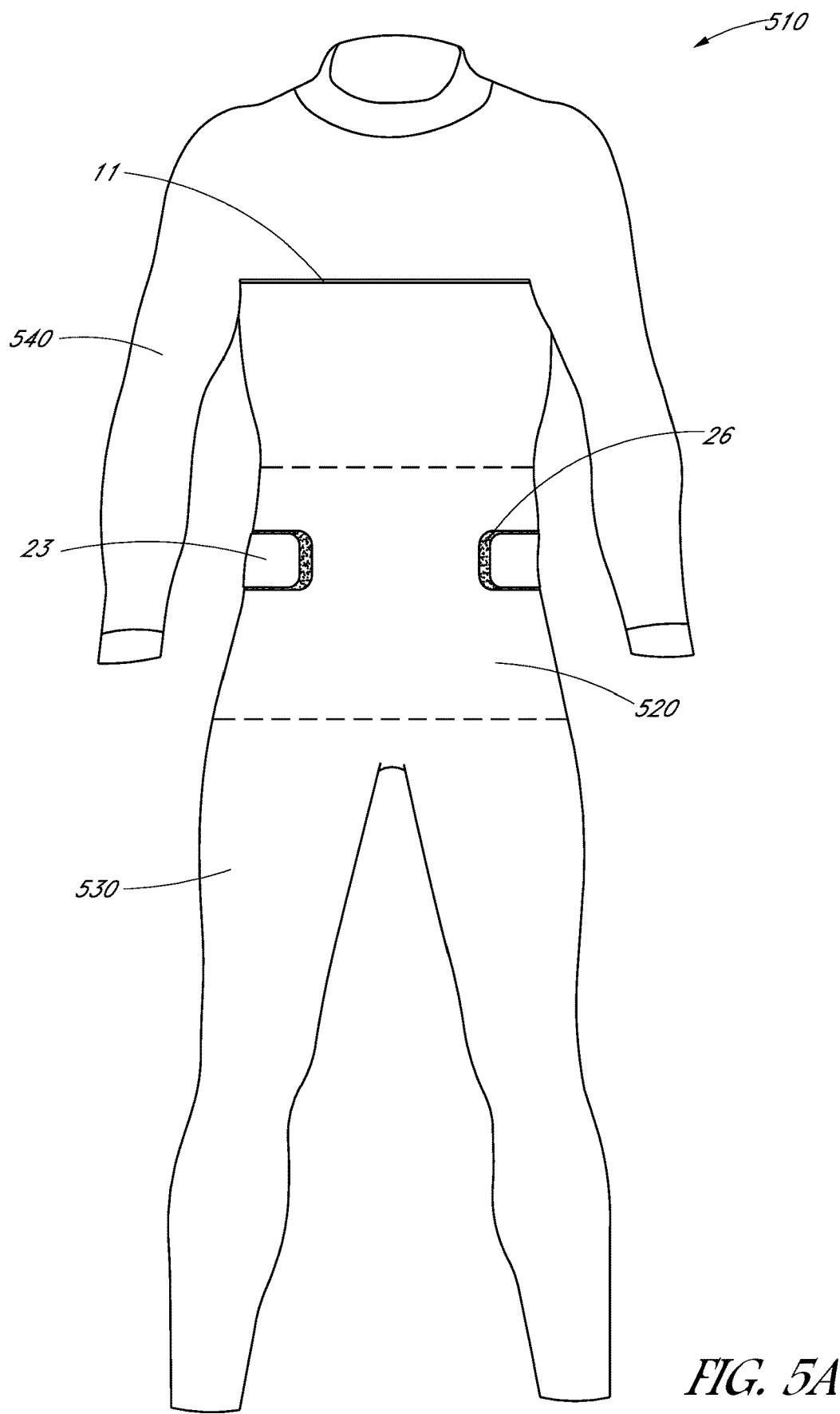
FIG. 5A is a front view of another embodiment of a wetsuit with one or more external straps and internal lumbar support features.

FIGS. 5A-5F illustrate an embodiment of a wetsuit 510 with one or more external straps 23 and internal lumbar support features. FIG. 5A shows a front view of the wetsuit 510. In certain embodiments, the wetsuit 510 can comprise one or more tensioning mechanisms. The at least one tensioning mechanism can comprise a strap 23. The lumbar portion 520 can comprise the one or more straps 23. The one or more straps 23 can be completely disposed outside the wetsuit 510. In certain embodiments, the one or more straps 23 wrap around more than the full circumference of the wetsuit 510. In certain embodiments, the one or more straps 23 comprise an elastic material. In certain embodiments, the one or more straps 23 can comprise wetsuit material. In certain embodiments, the one or more straps 23 can comprise one or more bands or straps of wetsuit material. In certain embodiments, the one or more straps 23 can comprise a substantially inelastic material.

The one or more straps 23 can comprise one or more securement mechanisms 26. In certain embodiments, each of the one or more straps 23 can comprise a central portion and one or more end portions. In certain embodiments, the one or more straps 23 comprise one or more right straps disposed on the right-hand side of the wetsuit 510 and one or more left straps disposed on the left-hand side of the wetsuit 510. In certain embodiments with right and left straps, the one or more straps 23 can each comprise a strap anchor portion 27, a central portion, and a securement mechanism 26. The one or more securement mechanisms 26 can be used to attach the one or more straps 23 to the outer surface of the lumbar portion 520 of the wetsuit 510. In certain embodiments, the one or more securement portions 26 are wings formed at the end of the one or more straps 23. Attaching the one or more straps 23 to the outer surface of the lumbar portion 520 of the wetsuit 510 can enable the one or more straps 23 to maintain tension on the lumbar portion 520. The one or more securement mechanisms 26 can substantially prevent the one or more straps 23 from moving once engaged. In certain embodiments, the outer surface of the lumbar portion 520 can have one or more portions that engage, interact, or mate with the one or more securement mechanisms 26. In certain embodiments where the one or more securement mechanisms 26 comprise Velcro, the one or more securement mechanisms 26 can comprise Velcro hooks. In certain embodiments where the one or more securement mechanisms 26 comprise the Velcro hooks, the one or more portions on the lumbar portion 520 can comprise the Velcro loops. The wearer can apply tension by changing the position of one or more end portions of the one or more straps 23. In some embodiments, the one or more straps 23 wrap around the entire circumference of the wetsuit 510. In certain embodiments, the one or more straps 23 wrap part of the way around the circumference of the wetsuit 510.

Figure 5B:
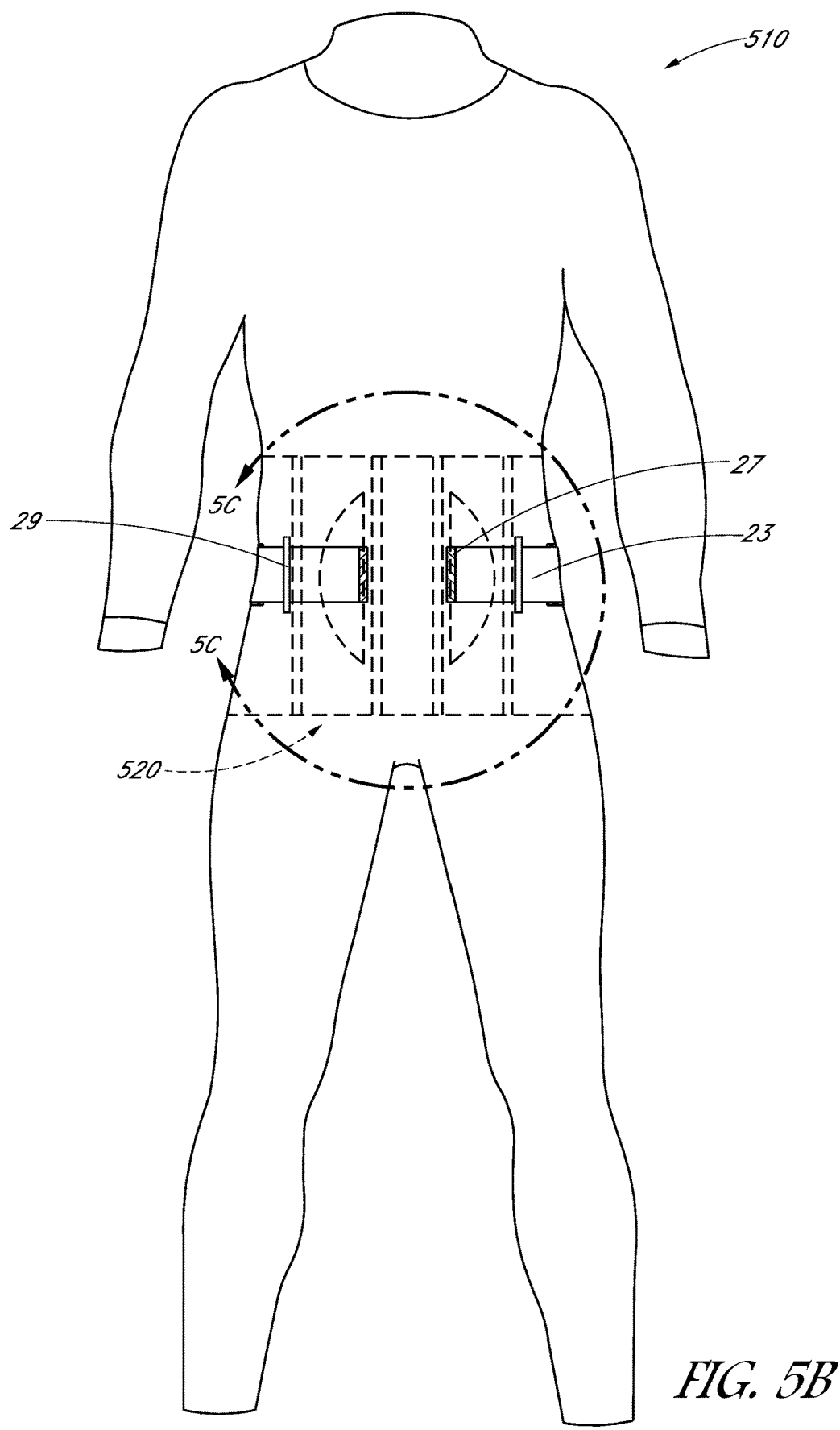
FIG. 5B is a back view of the wetsuit in FIG. 5A with inner components shown in dashed lines.
Figure 5C:
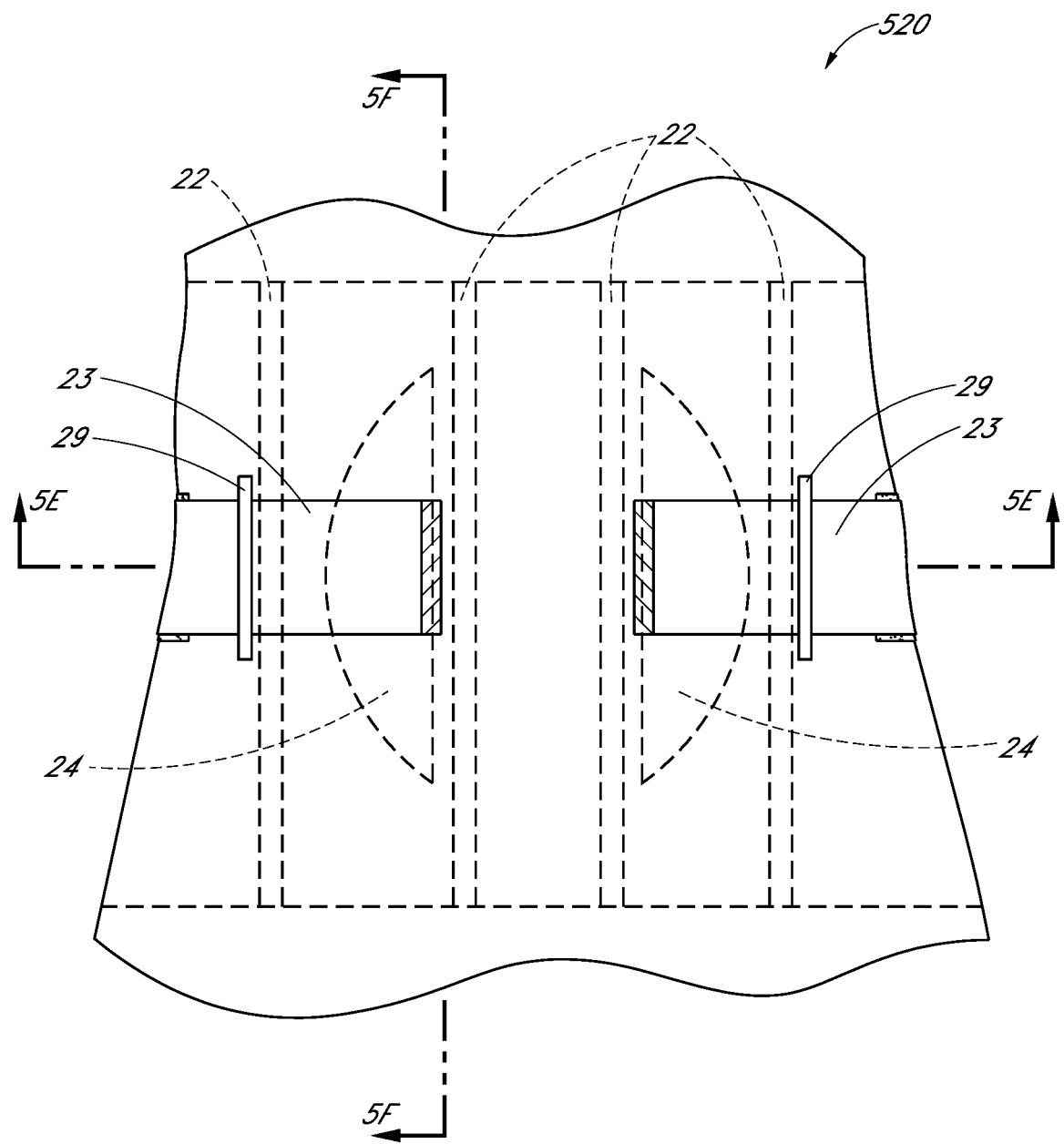
FIG. 5C is a close-up view of the lumbar portion of the wetsuit of FIG. 5B encircled by line 5C-5C.

FIG. 5B shows a back view of the wetsuit 510 in FIG. 5A with inside components shown in dashed lines. FIG. 5C shows a close-up view of the lumbar portion 520 of the wetsuit 510 of FIG. 5B encircled by line 5C-5C. Inner components are shown in dashed lines in FIGS. 5B and 5C. In certain embodiments, the one or more straps 23 can comprise one or more strap anchor portions 27. In certain embodiments, the one or more strap anchor portions 27 can be disposed on the opposite end of the one or more straps 23 from the one or more securement mechanisms 26. In certain embodiments, the one or more strap anchor portions 27 can be permanently attached to the outer surface of the wetsuit 510. In certain embodiments, the one or more strap anchor portions 27 can be integral with the wetsuit 510 so that the one or more straps 23 are formed with the wetsuit 510. The one or more strap anchor portions 27 can be attached to the wetsuit 510 in ways that include but are not limited to using glue, stitching, liquid seams, bonding, other ways of chemical or mechanical joining or some combination thereof. In certain embodiments, the one or more strap anchor portions 27 can be embedded in the wetsuit material. In certain embodiments, the one or more strap anchor portions 27 can be removably connected to an outer surface of the wetsuit 510. One of skill in the art will recognize that the one or more strap anchor portions 27 can comprise a variety of different mechanisms which can include, but are not limited to Velcro, buttons, magnets, friction locks, or some other mechanical locking device. In this embodiment, the strap 23 runs from posterior to anterior. In certain embodiments, the one or more straps 23 can run from anterior to posterior. In certain embodiments, the one or more strap anchor portions 27 can be disposed on the anterior or side portions of the wetsuit 510 and the one or more securement mechanisms 26 can be disposed on the posterior portion of the wetsuit 510. Additionally, the wetsuit 510 can comprise one or more straps 23 running from posterior to anterior and one or more straps 23 running from anterior to posterior.

In some embodiments, the wetsuit 510 can comprise one or more belt loops 29. The one or more belt loops 29 can retain the one or more straps 23. By retaining the one or more straps 23, the one or more belt loops 29 can prevent at least a portion of the one or more straps 23 from dangling from the one or more strap anchor portions 27. In embodiments where there is a single strap 23, the one or more belt loops 29 can prevent the single strap 23 from falling off of the wetsuit 510 when the one or more securement mechanisms 26 are not securing the one or more straps 23 to the wetsuit 510.

The lumbar portion 520 can comprise one or more struts 22. In certain embodiments, the one or more struts 22 can be arranged vertically. The one or more struts 22 can run from the top of the lumbar portion 520 to the bottom. In some embodiments, the one or more struts 22 can also be arranged to span only a portion of the lumbar portion 520. The one or more struts 22 can extend at least partially across the lumbosacral and/or paravertebral lumbar area. The one or more struts 22 can apply pressure on the muscles in the lumbosacral and/or paravertebral lumbar area. This pressure may alleviate strain on muscles in the lumbosacral and/or paravertebral lumbar area. A person of skill in the art will recognize that the one or more struts 22 can be made from many different substantially rigid materials including, but not limited to high-density polyethylene, other similar materials, other plastics, metals, metal alloys, polymers, or some combination thereof.

In certain embodiments, the lumbar portion 520 comprises one or more pressure pads 24. In certain embodiments, the one or more pressure pads 24 can be coupled to the one or more straps 23. The one or more pressure pads 24 can run from the top of the lumbar portion 520 to the bottom. In some embodiments, the one or more pressure pads 24 can also be arranged to span only a portion of the lumbar portion 520. The one or more pressure pads 24 can extend at least partially across the lumbosacral and/or paravertebral lumbar area. In certain embodiments, when the one or more straps 23 are tensioned, the one or more pressure pads 24 can apply pressure to the muscles in the lumbosacral and/or paravertebral lumbar area. In certain embodiments, the one or more pressure pads 24 are located in line with the one or more struts 22. The one or more pressure pads 24 can be disposed between the one or more struts 22. In certain embodiments, the one or more pressure pads 24 are spaced apart along a length of the lumbar portion 520. In certain embodiments, the one or more pressure pads 24 can be disposed on the inner side of the one or more struts 22. In some embodiments, the one or more pressure pads 24 can be disposed between the one or more struts 22 and the one or more straps 23. In certain embodiments, the one or more pressure pads 24 can be disposed on the outer side of both the one or more struts 22 and the one or more straps 23. In certain embodiments, the one or more pressure pads 24 can be arranged vertically. In certain embodiments, the one or more pressure pads 24 can be arranged horizontally. In certain embodiments, the one or more pressure pads 24 can be arranged at some angle in between vertical and horizontal. In certain embodiments, the one or more pressure pads 24 can extend along the entire vertical, horizontal, or angled length of the lumbar portion 520. The one or more pressure pads 24 can be made from a variety of different materials including but not limited to foams, rubbers, latexes, or some combination thereof. In some embodiments, the one or more pressure pads 24 can be or can include pockets filled with air. The pockets filled with air can allow for the amount of air inside the pockets to be adjustable. In embodiments where the one or more pressure pads 24 are or include pockets filled with air, the one or more pressure pads 24 can provide extra buoyancy for the person wearing the wetsuit 510. In certain embodiments, the one or more pressure pads 24 can be disposed in the curve of the small of the back.

Figure 5D:
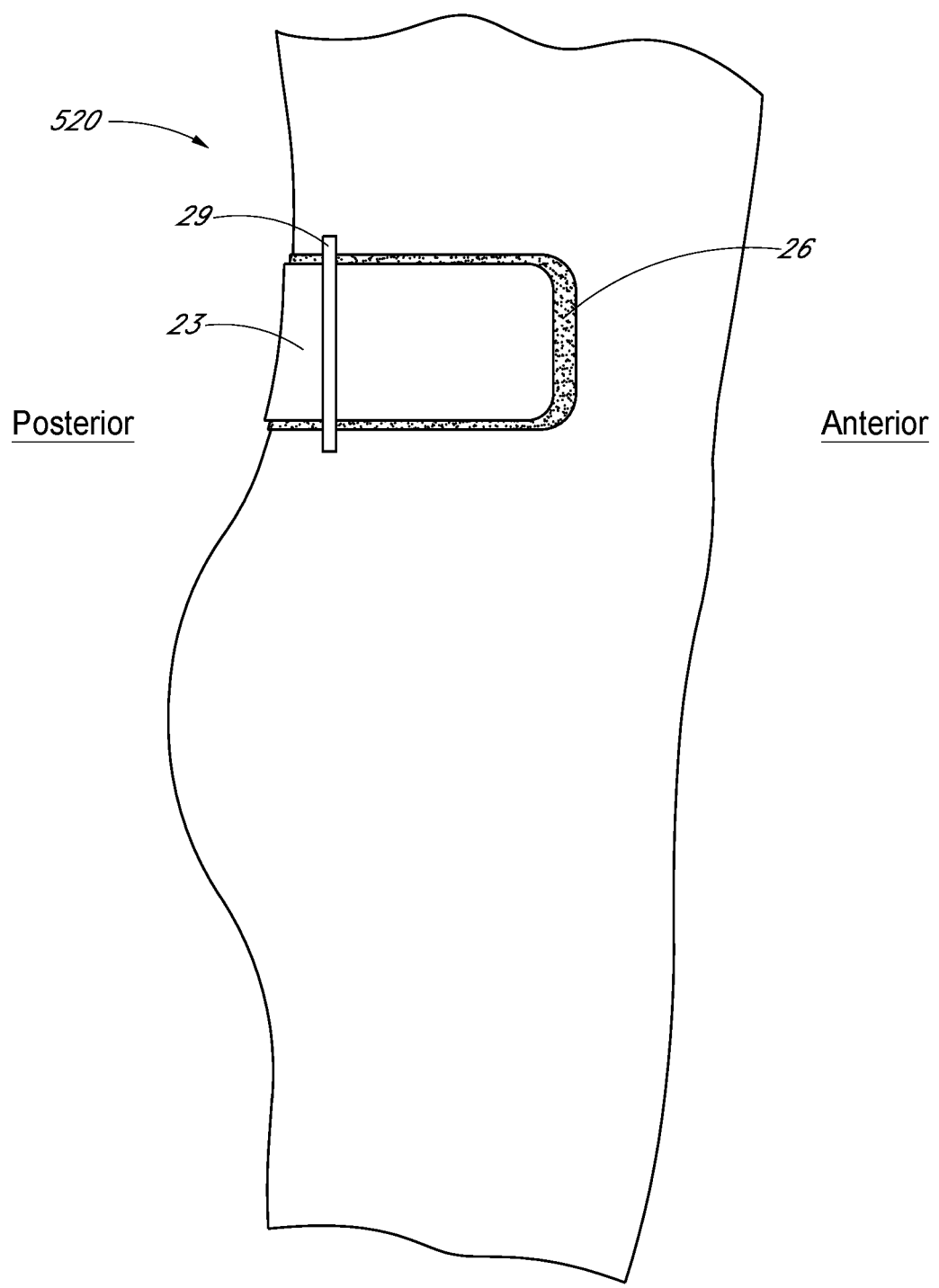
FIG. 5D is a right-side view of the wetsuit in FIG. 5A.

FIG. 5D shows a partial right-side view of the wetsuit 510 in FIG. 5A. In certain embodiments, the one or more belt loops 29 are on both the right and left sides of the wetsuit 510. In certain embodiments, the one or more straps 23 may terminate before they reach the anterior portion. This configuration can prevent discomfort due to having one or more straps 23 or one or more securement mechanisms 26 disposed on the stomach portion of the wetsuit where the wearer may end up lying on them. In configurations with one or more straps 23 running both posteriorly to anteriorly and anteriorly to posteriorly, the one or more straps 23 running from anterior to posterior may comprise a strap anchor portion 27 disposed on the sides of the lumbar portion 520 at a location proximate to where the securement mechanisms 26 is in FIG. 5D. In some embodiments, the right-side view of the wetsuit 510 is substantially symmetrical to the left-side view of the wetsuit 510. In some embodiments, the right-side view of the wetsuit 510 is not substantially symmetrical to the left-side view of the wetsuit 510.

Figure 5E:
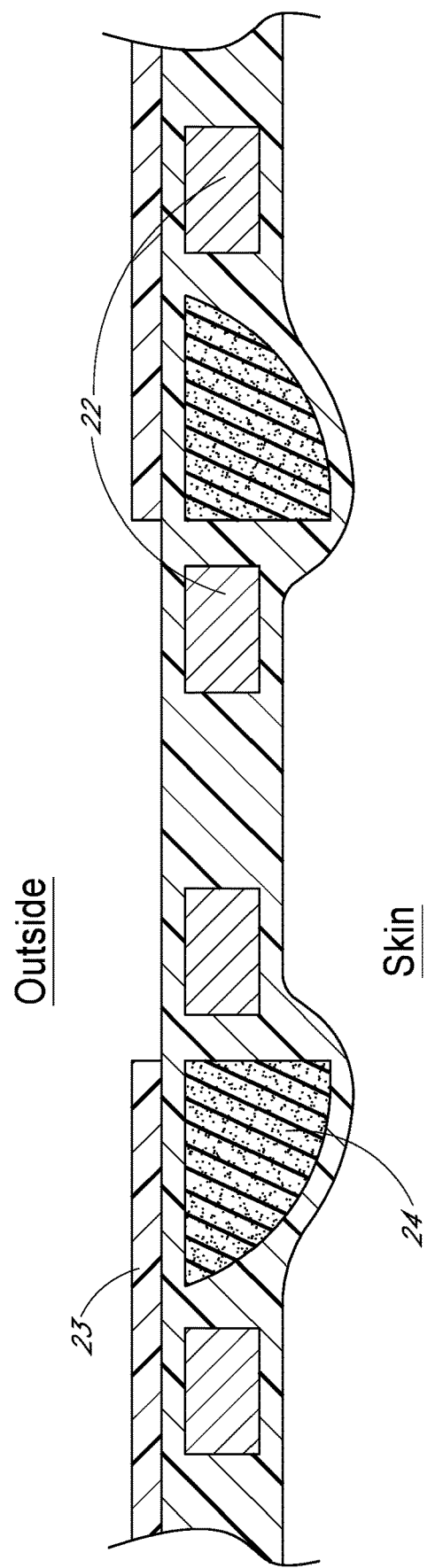
FIG. 5E is a horizontal cross-sectional view of the lumbar portion of FIG. 5C taken along line 5E-5E.
Figure 5F:
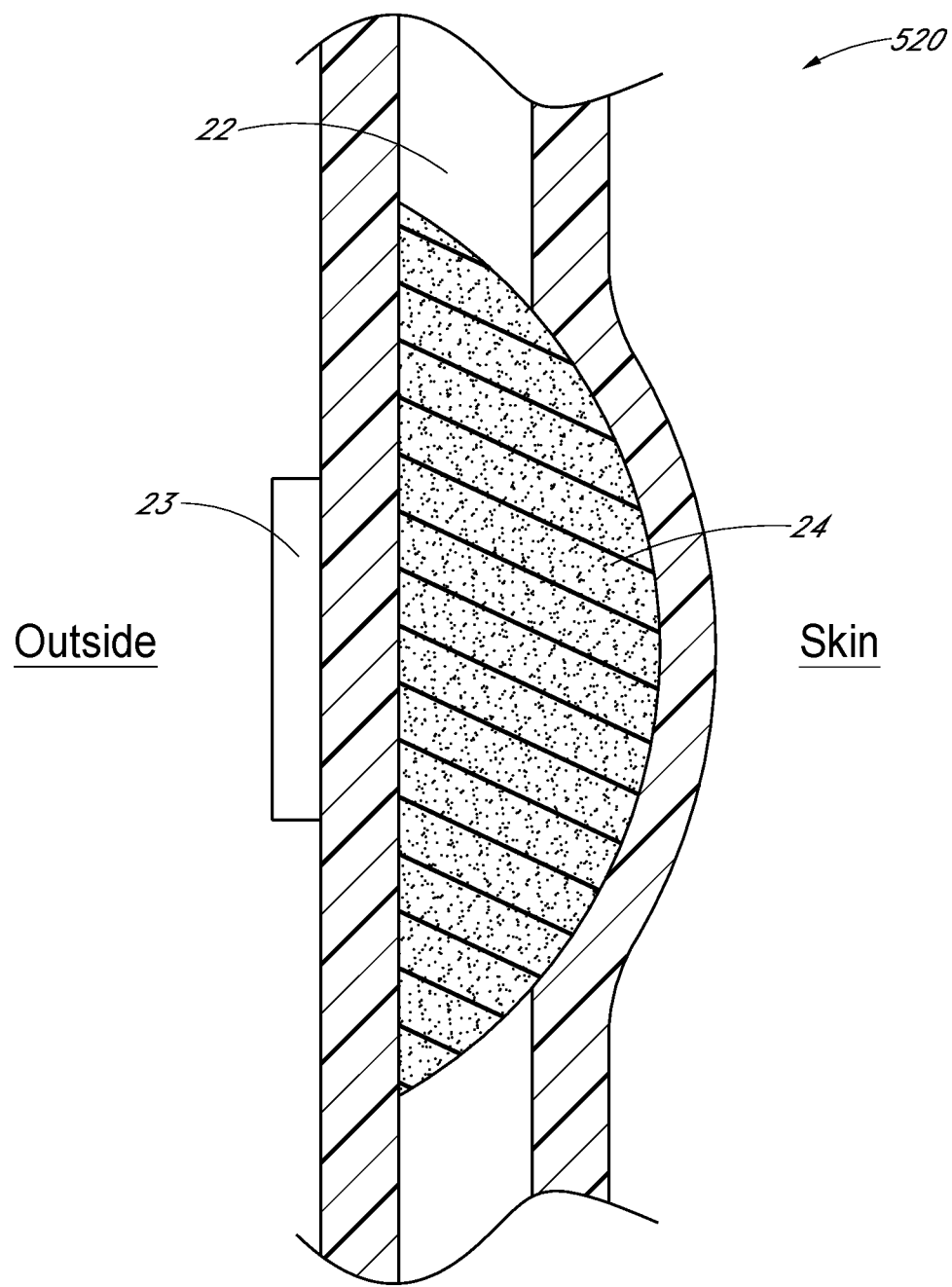
FIG. 5F is a vertical cross-sectional view of the lumbar portion of FIG. 5C taken along line 5F-5F.

FIG. 5E shows a cross-sectional view of one embodiment of the wetsuit 510 taken through the line 5E-5E in FIG. 5C. FIG. 5E shows lumbar supportive components integrated into the wetsuit 510 with straps 23 attached to the outer surface of the lumbar portion 520. FIG. 5F shows a cross-sectional view of one embodiment of the wetsuit 510 taken through the line 5F-5F in FIG. 5C. Though not shown in the figures, in certain embodiments, the one or more struts 22 can be disposed on the inside or outside of the foam rubber or other wetsuit material. In embodiments where the one or more struts 22 are arranged on the inside or outside of the foam rubber or other wetsuit material, the one or more struts 22, one or more straps 23, and/or one or more pressure pads 24 can be removably integrated into the wetsuit 510. In certain embodiments, a band of wetsuit material connects to the one or more struts 22, the one or more straps 23, and/or the one or more pressure pads 24. In certain embodiments, a band or large strap of wetsuit material may enable the one or more struts 22, the one or more straps 23, and/or the one or more pressure pads 24 to be removed and/or interchanged more easily. The one or more struts 22, the one or more straps 23, and/or the one or more pressure pads 24 can also be arranged in between two separate layers of foam rubber or another wetsuit material.

Figure 6A:
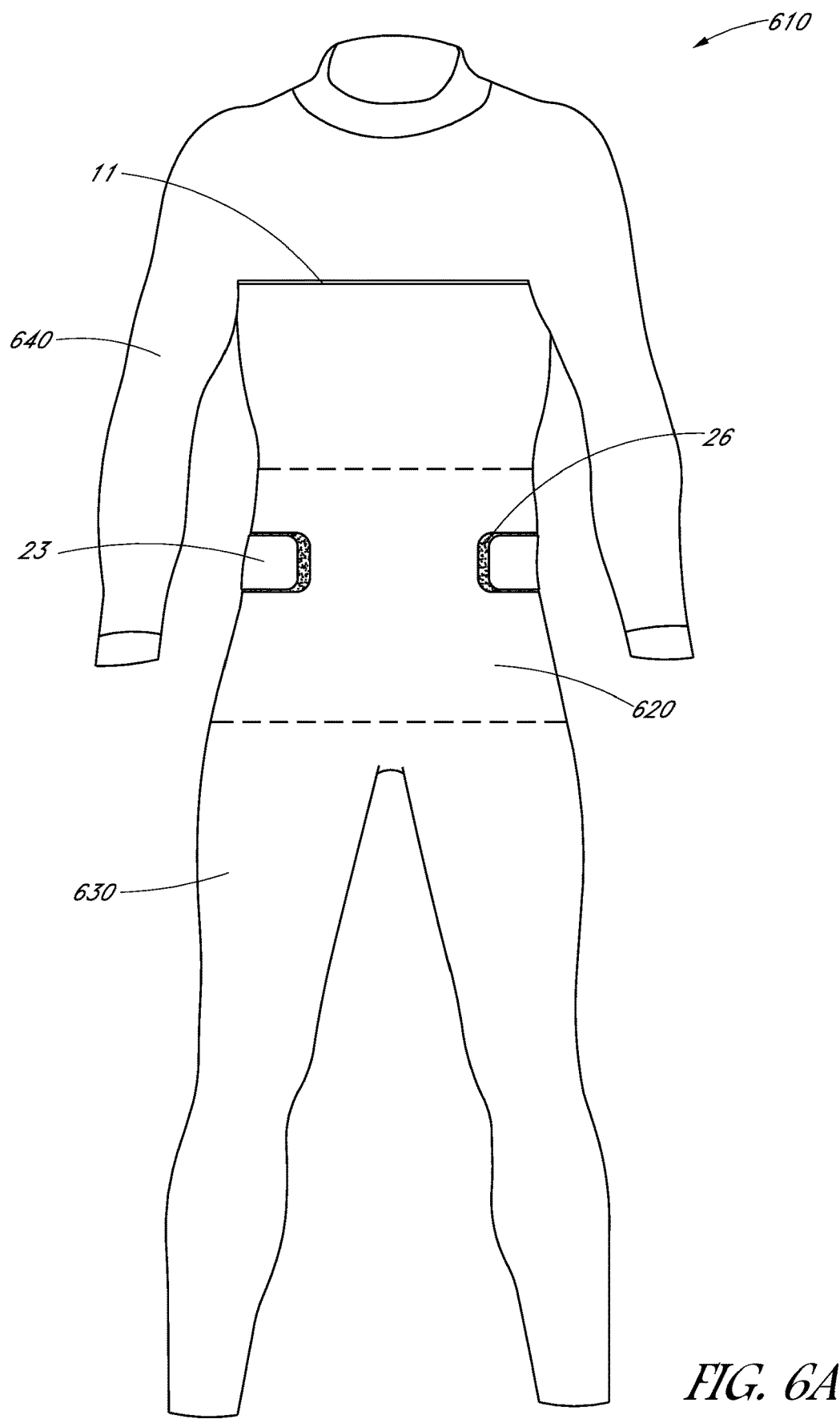
FIG. 6A is a front view of another embodiment of a wetsuit having a partially-internal strap and lumbar support features.

FIGS. 6A-6F illustrate an embodiment of a wetsuit 610 having a partially-internal strap 23 and lumbar support features. FIG. 6A shows a front view of an embodiment of a wetsuit 610 having a partially-internal strap 23 and lumbar support features. In certain embodiments, the wetsuit 610 can include at least one tensioning mechanism. The at least one tensioning mechanism can comprise a strap 23. The lumbar portion 620 can comprise one or more straps 23. The one or more straps 23 can allow the wearer to selectively change a level of the support provided to the lumbosacral region of the wearer by the lumbar portion 620.

Figure 6B:
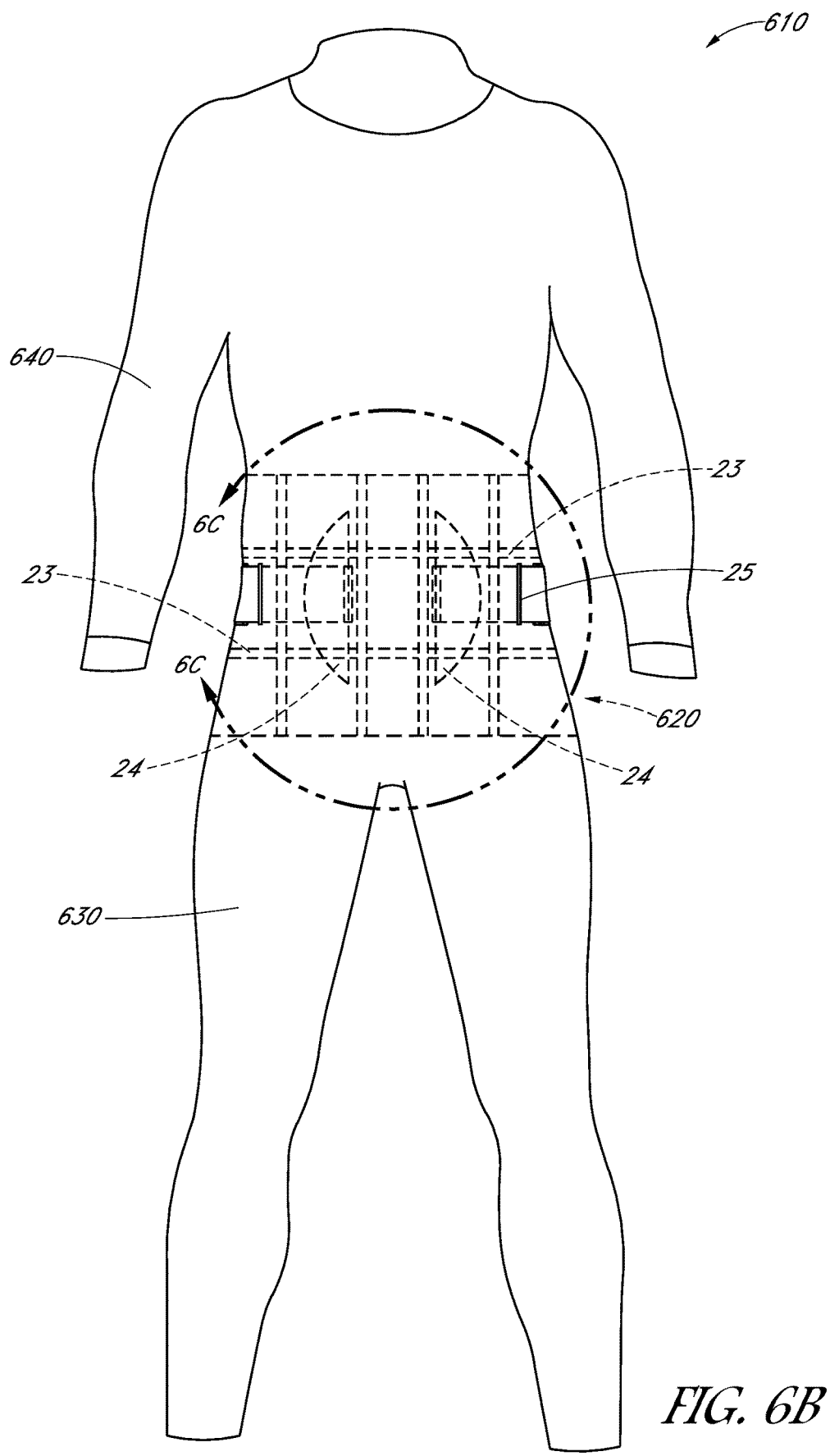
FIG. 6B is a back view of the wetsuit of FIG. 6A showing inner components of the lumbar support features of the lumbar portion in dashed lines.

FIG. 6B is a back view of the wetsuit 610 of FIG. 6A. In certain embodiments, there are one or more openings 25 in the wetsuit 610. The one or more openings 25 can be located on the lumbar portion 620. In certain embodiments, the one or more openings 25 are located on an upper portion 640 of the wetsuit 610. In certain embodiments, one or more straps 23 pass through the one or more openings 25. The one or more securement mechanisms 26 can be disposed in or near to the one or more openings 25. For example, in certain embodiments the one or more openings 25 can be plastic rings or rectangles through which the one or more straps 23 pass. In certain embodiments, the one or more securement mechanisms 26 can clamp down on the one or more straps 23 to prevent movement. In certain embodiments, the one or more securement mechanisms 26 can prevent movement of the one or more straps 23 by providing friction between the one or more straps 23 and the one or more securement mechanisms 26. In some embodiments, the one or more openings 25 can have one or more gaskets or seals. The one or more gaskets or seals can allow the one or more straps 23 to pass through one or more openings 25 while significantly preventing additional water from flowing into the wetsuit 610.

Figure 6C:
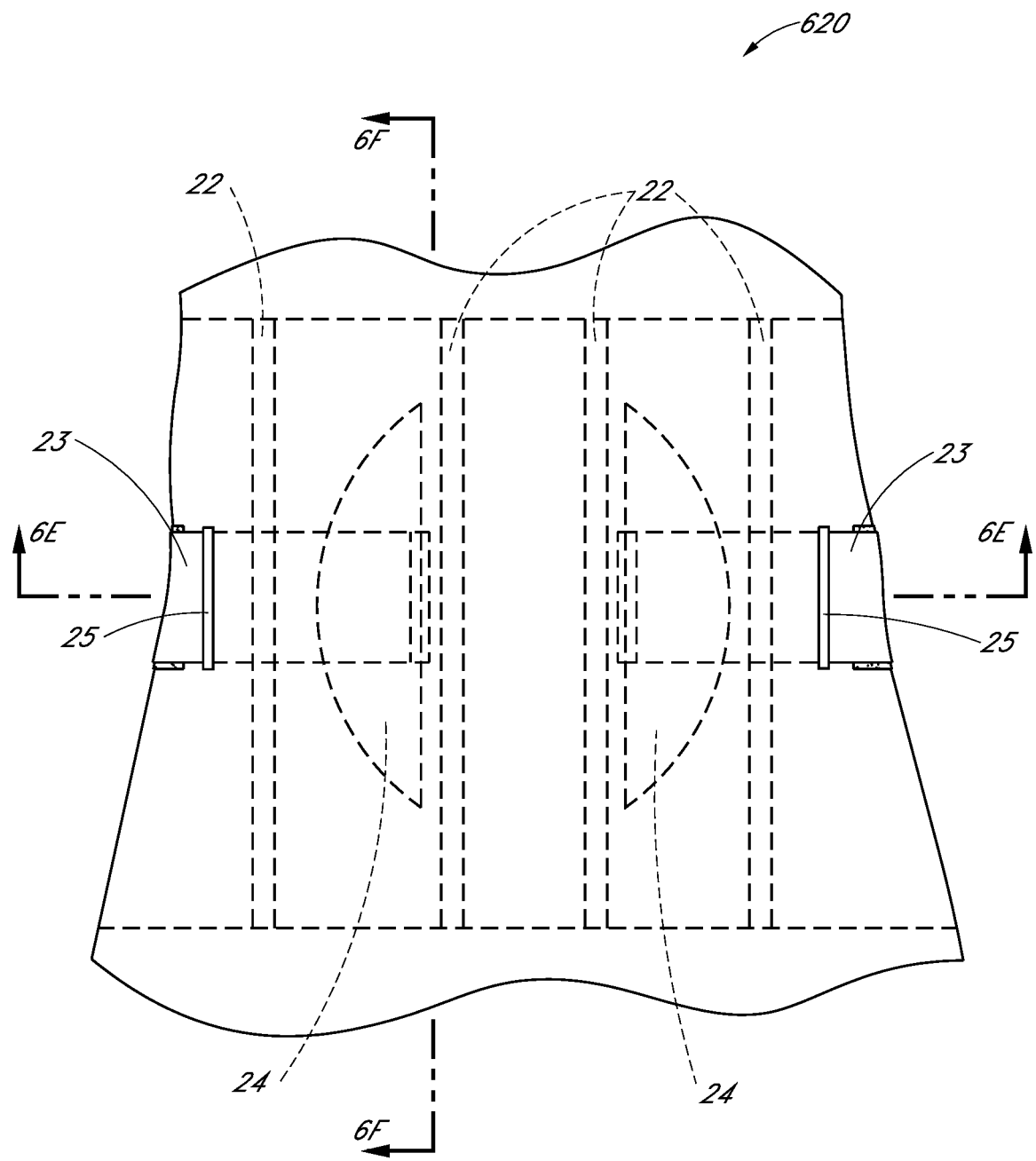
FIG. 6C is a close-up view of the lumbar portion of FIG. 6B encircled by line 6C-6C.
Figure 6D:
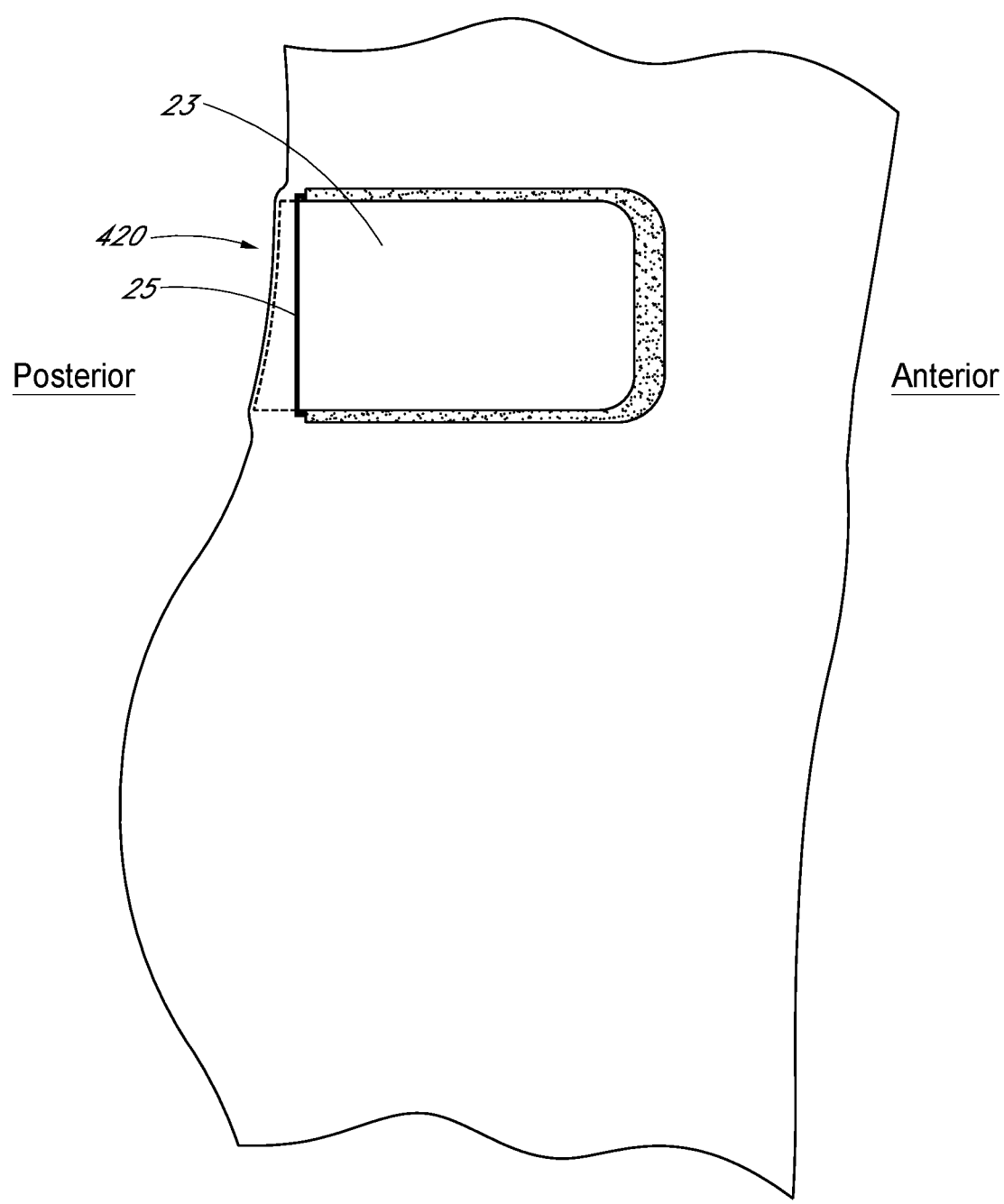
FIG. 6D is a partial right-side view of the wetsuit from FIG. 6A.

FIG. 6C is a close-up view of the lumbar portion 620 of FIG. 6B encircled by line 6C-6C. Inner components are shown in dashed lines in FIGS. 6B and 6C. FIG. 6D shows a partial right-side view of the wetsuit 610. Inner components are also shown in dashed lines in FIGS. 6C and 6D. In some embodiments, the right-side view of the wetsuit 610 is substantially symmetrical to the left-side view of the wetsuit 610. In some embodiments, the right-side view of the wetsuit 610 is not substantially symmetrical to the left-side view of the wetsuit 610.

Figure 6E:
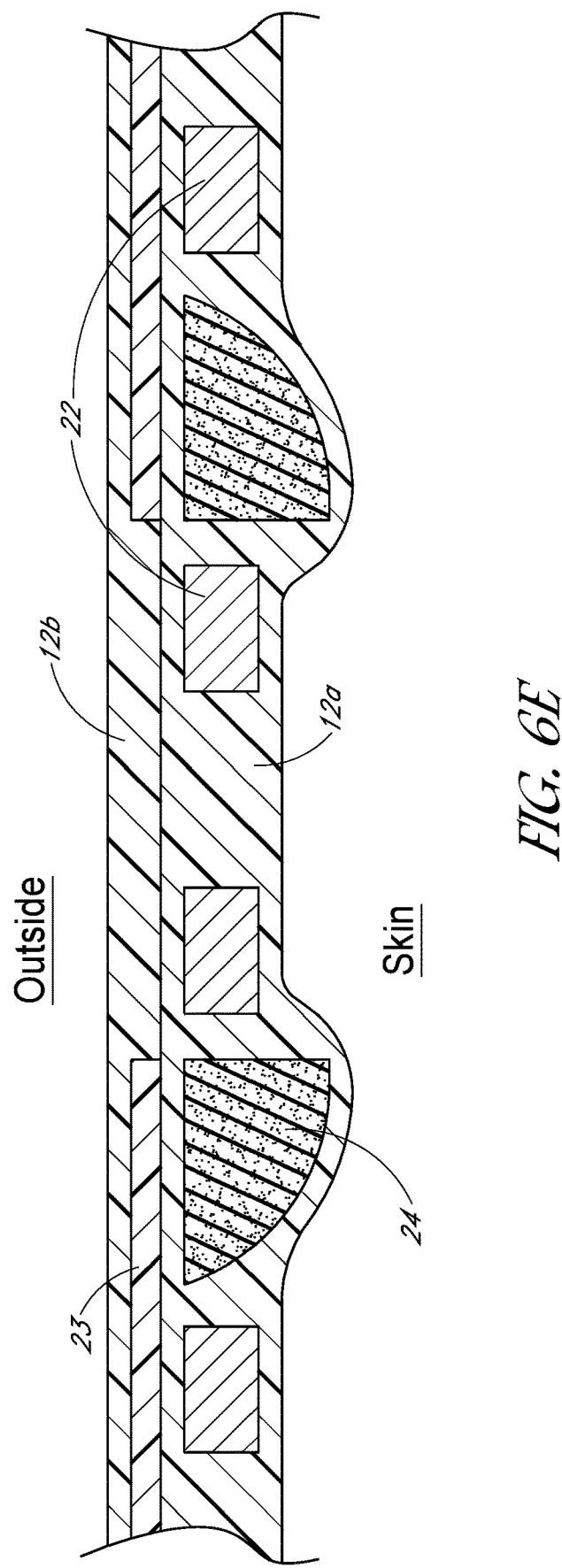
FIG. 6E is a horizontal cross-sectional view of the lumbar portion of FIG. 6C taken at line 6E-6E.
Figure 6F:
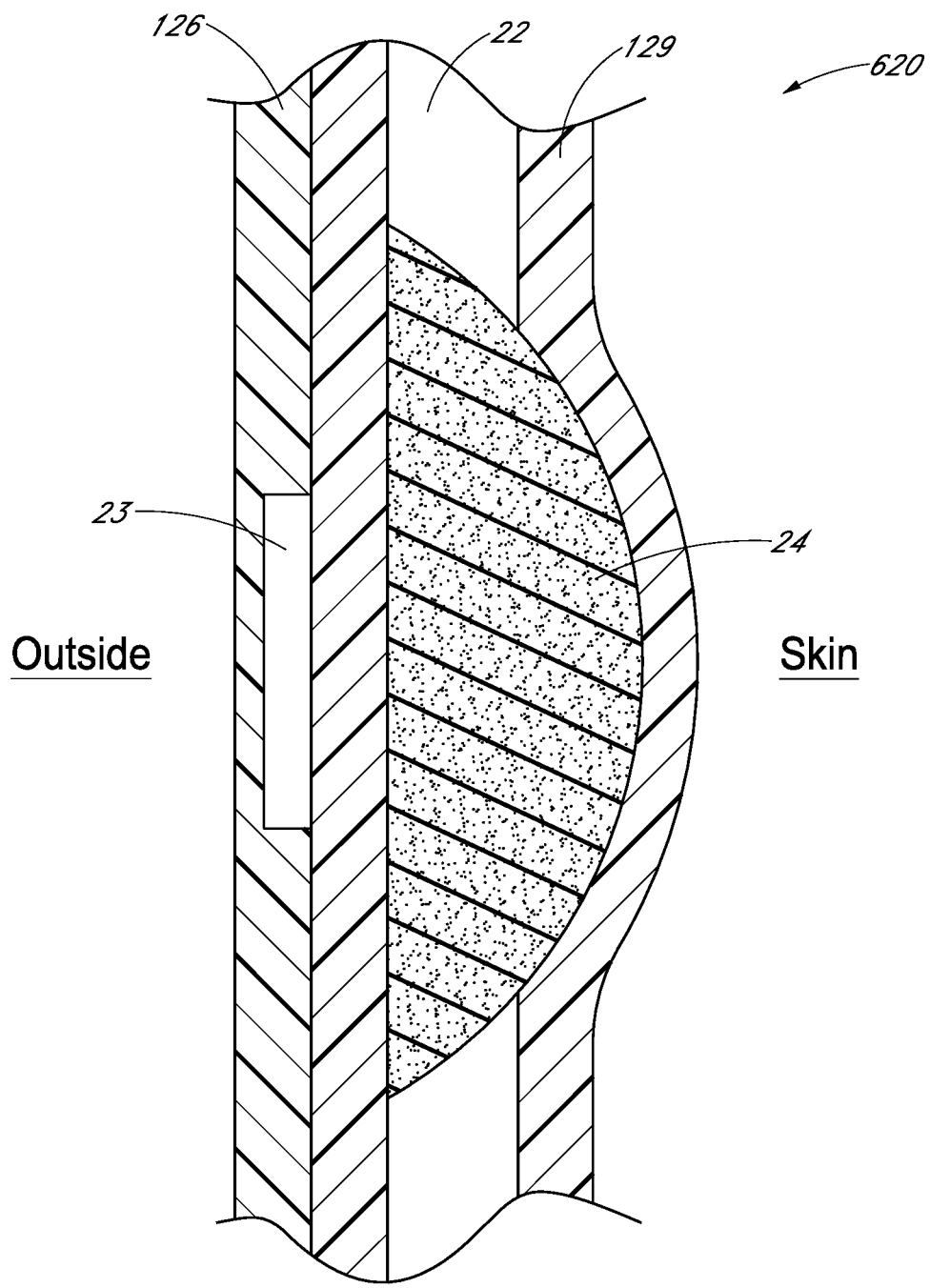
FIG. 6F is a vertical cross-sectional view of the lumbar portion of FIG. 6C taken at line 6F-6F.

FIG. 6E shows a horizontal cross-sectional view of the lumbar portion 620 of FIG. 6C taken at line 6E-6E. FIG. 6F shows a vertical cross-sectional view of the lumbar portion 620 of FIG. 6C taken at line 6F-6F. The lumbar portion 620 can comprise one or more straps 23. In certain embodiments, each of the one or more straps 23 can comprise a central portion and one or more end portions. In certain embodiments, the one or more end portions pass through at least one layer of the wetsuit material. In some embodiments, the one or more end portions pass through the entire thickness of the wetsuit 610 from the inside to the outside or vice versa as shown in FIG. 6D. In certain embodiments, the central portions of each strap 23 can terminate in the lumbar portion 620 so that the central portion of one strap 23 does not connect to the central portion of another strap 23 as shown in FIG. 6E. In certain embodiments, the central portion of each strap 23 is anchored in a first layer of wetsuit material 12a. In certain embodiments, the central portion of each strap 23 is anchored in a second layer of wetsuit material 12b. In certain embodiments, the central portion of each strap 23 is anchored between two layers of wetsuit material 12a & 12b. In embodiments where the one or more end portions of the one or more straps 23 have a portion located outside of the wetsuit 610, those one or more end portions can be used by the wearer to tension the lumbar portion 620. The wearer applies tension to the one or more end portions of the one or more straps 23. The wearer can apply tension by changing the position of one or more end portions of the one or more straps 23. In some embodiments, the wetsuit 610 can comprise one or more securement mechanisms 26. In some embodiments, the one or more straps 23 can have one or more securement mechanisms 26. In some embodiments, the one or more securement mechanisms 26 can comprise Velcro hooks on the strap 23 and Velcro loops on the sides of the lumbar portion 620 as shown in FIG. 6D. In some embodiments, the one or more straps 23 wrap around the entire circumference of the wetsuit 610. In certain embodiments, the one or more straps 23 wrap part of the way around the circumference of the wetsuit 610. In certain embodiments, the one or more straps 23 wrap around more than the full circumference of the wetsuit 610. One of skill in the art will recognize that the one or more securement mechanism 26 can be a variety of different mechanisms used to prevent the one or more straps 23 from moving substantially which can include, but are not limited to Velcro, buttons, magnets, friction locks, or some other mechanical locking device.

The one or more straps 23 can terminate on the outside of the wetsuit 610 so that the tension can be adjusted from the outside of the wetsuit 610. In certain embodiments, the one or more straps 23 are arranged horizontally. In some embodiments, at least one of the one or more straps 23 is arranged vertically. In some embodiments, at least one of the one or more straps 23 is arranged at an angle between vertical and horizontal. In certain embodiments, the one or more straps 23 comprise an elastic material. In certain embodiments, the one or more straps 23 can comprise wetsuit material. For example, the wetsuit material can have the shape of a large strap or band. In certain embodiments, the one or more straps 23 can comprise one or more bands or straps of wetsuit material. In certain embodiments, the one or more straps 23 can be integral with the wetsuit 610 so that the one or more straps 23 are formed with the wetsuit 610. In certain embodiments, the one or more straps 23 can comprise a substantially inelastic material. A person of skill in the art will recognize that the one or more straps 23 can be made from many different materials including, but not limited to Neoprene, polyesters, natural or synthetic rubbers, latexes, vinyl, nylons, low-density polyethylene, or other plastics, polymers, or some combination thereof.

The lumbar portion 620 can comprise one or more struts 22. In certain embodiments, the one or more struts can be arranged vertically. The one or more struts 22 can run from the top of the lumbar portion 620 to the bottom. In some embodiments, the one or more struts 22 can also be arranged to span only a portion of the lumbar portion 620. The one or more struts 22 can extend at least partially across the lumbosacral and/or paravertebral lumbar area. In some embodiments, the one or more struts 22 can be disposed adjacent to the one or more straps 23. In certain embodiments, the one or more struts 22 can be coupled to the one or more straps 23. The one or more straps 23 can be arranged horizontally around the back of the wetsuit 610. In some embodiments, the one or more struts 22 are not directly connected to the one or more straps 23. In certain embodiments, the one or more straps 23 can be used to apply tension to the one or more struts 22. The one or more struts 22 can transfer tension into pressure on the muscles in the lumbosacral and/or paravertebral lumbar area. In certain embodiments, the one or more straps 23 can be used to apply tension to the lumbar portion 620. This tension can in turn apply pressure to the muscles in the lumbosacral and/or paravertebral lumbar area. This pressure may alleviate strain on muscles in the lumbosacral and/or paravertebral lumbar area.

In certain embodiments, an internal or external tensioning mechanism can be used to apply or transfer tension to the one or more straps 23. This tensioning mechanism can be composed of elastic straps, wires, gearing, pulleys, ratchets, and/or various other types of mechanical or electrical tensioners. In certain embodiments, a tensioning mechanism is connected to a dial on the outside of the wetsuit 610. The dial could be used to increase and decrease the tension of the one or more straps 23. In certain embodiments, the one or more straps 23 can be the tensioning mechanisms. The one or more straps 23 can be tensioned by their own elasticity. The one or more straps 23 can be tensioned by being secured in a taught position.

In certain embodiments, the lumbar portion 620 comprises one or more pressure pads 24. In certain embodiments, the one or more pressure pads 24 can be coupled to the one or more straps 23. The one or more pressure pads 24 can run from the top of the lumbar portion 620 to the bottom. In some embodiments, the one or more pressure pads 24 can also be arranged to span only a portion of the lumbar portion 620. The one or more pressure pads 24 can extend at least partially across the lumbosacral and/or paravertebral lumbar area. In certain embodiments, when the one or more straps 23 are tensioned, the one or more pressure pads 24 can apply pressure to the muscles in the lumbosacral and/or paravertebral lumbar area. In certain embodiments, the one or more pressure pads 24 are located in line with the one or more struts 22. The one or more pressure pads 24 can be disposed between the one or more struts 22. In certain embodiments, the one or more pressure pads 24 are spaced apart along a length of the lumbar portion 620. In certain embodiments, the one or more pressure pads 24 can be disposed on the inner side of the one or more struts 22. In some embodiments, the one or more pressure pads 24 can be disposed between the one or more struts 22 and the one or more straps 23. In certain embodiments, the one or more pressure pads 24 can be disposed on the outer side of both the one or more struts 22 and the one or more straps 23. In certain embodiments, the one or more pressure pads 24 can be arranged vertically. In certain embodiments, the one or more pressure pads 24 can be arranged horizontally. In certain embodiments, the one or more pressure pads 24 can be arranged at some angle in between vertical and horizontal. In certain embodiments, the one or more pressure pads 24 can extend along the entire vertical, horizontal, or angled length of the lumbar portion 620. The one or more pressure pads 24 can be made from a variety of different materials including but not limited to foams, rubbers, latexes, or some combination thereof. In some embodiments, the one or more pressure pads 24 can be or can include pockets filled with air. The pockets filled with air can allow for the amount of air inside the pockets to be adjustable. In embodiments where the one or more pressure pads 24 are or include pockets filled with air, the one or more pressure pads 24 can provide extra buoyancy for the person wearing the wetsuit 610. In certain embodiments, the one or more pressure pads 24 can be disposed in the curve of the small of the back.

In certain embodiments, the one or more straps 23 are located on the outer side of the one or more struts 22. The one or more straps 23 can provide tension onto the one or more struts 22. In certain embodiments, the one or more straps 23 are located on the inner side of the one or more struts 22. In certain embodiments, the one or more straps 23 are arranged on both the outer and inner sides of the one or more struts 22. In certain embodiments where the one or more straps 23 are arranged on the outer and inner sides of the one or more struts 22, the one or more straps 23 on each side may then converge from the central portion of the one or more straps 23 to form a single strap 23 towards the end portion of the one or more strap 23. In embodiments where there is more than one straps 23, the straps 23 can converge to form fewer straps 23 or a single strap 23 toward the end portions of the straps 23.

In certain embodiments with multiple straps 23, the straps 23 can be evenly spaced. In certain embodiments with multiple straps 23, the straps 23 can be placed strategically to provide optimal amount of pressure on the lumbosacral and/or paravertebral lumbar area. In certain embodiments, there can be no straps 23. In certain embodiments with no straps 23, the one or more struts 22 or one or more pressure pads 24 can be embedded within the wetsuit 610. In certain embodiments with no straps 23, tensioning can be accomplished by using the wetsuit material of the lumbar portion 620. Additionally, in some embodiments, there can be no struts 22. In some embodiments, there can be no pressure pads 24. In some embodiments, the one or more struts 22 can be replaced by one or more pressure pads 24.

In certain embodiments, the one or more straps 23 can comprise one or more strap anchor portions 27. In certain embodiments, the one or more strap anchor portions 27 can be disposed on the opposite end of the one or more straps 23 as the one or more securement mechanisms 26. In certain embodiments, the one or more strap anchor portions 27 can be integral with the wetsuit 610 so that the one or more straps 23 are formed with the wetsuit 610. The one or more strap anchor portions 27 can be attached to the wetsuit 610 in ways that include but are not limited to using glue, stitching, liquid seams, bonding, other ways of chemical or mechanical joining or some combination thereof. In certain embodiments, the one or more strap anchor portions 27 can be embedded in the wetsuit material. One of skill in the art will recognize that the one or more strap anchor portions 27 can comprise a variety of different mechanisms which can include, but are not limited to Velcro, buttons, magnets, friction locks, or some other mechanical locking device. In this embodiment, the strap 23 runs from posterior to anterior. In certain embodiments, the one or more straps 23 can run from anterior to posterior. In certain embodiments, the one or more strap anchor portions 27 can be disposed on the anterior or side portions of the wetsuit 610 and the one or more securement mechanisms 26 can be disposed on the posterior portion of the wetsuit 610. Additionally, the wetsuit 610 can comprise one or more straps 23 running from posterior to anterior and one or more straps 23 running from anterior to posterior.

Figures 7A, 7B:
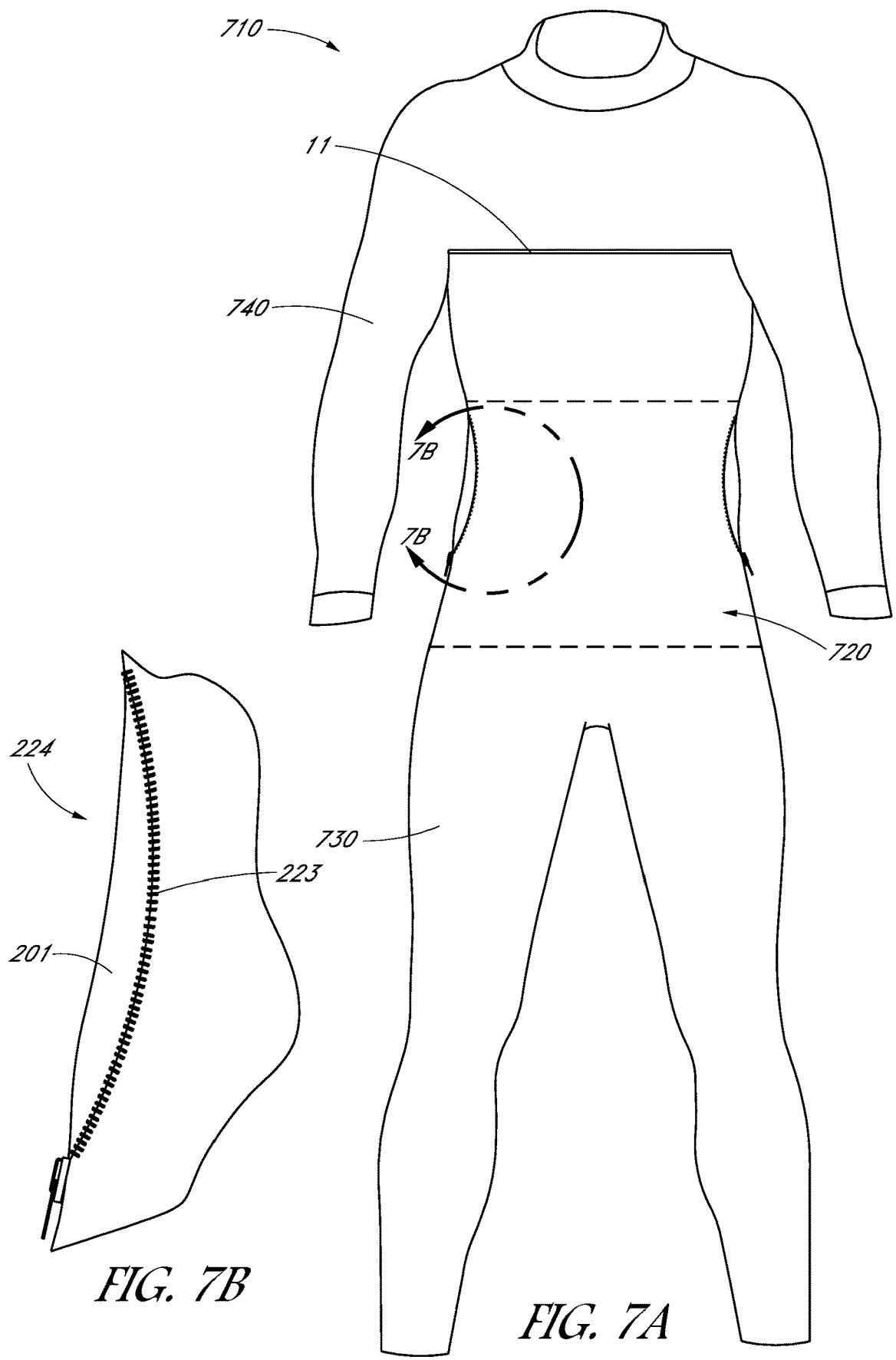
FIG. 7A is a front view of another embodiment of a wetsuit with a lumbar portion that utilizes tensioning fasteners and lumbar support features.
FIG. 7B is a close-up view of a portion of the wetsuit in FIG. 7A encircled by line 7B-7B.

FIGS. 7A-7H illustrate an embodiment of a wetsuit 710 with a lumbar portion 720 that comprises one or more tensioning mechanisms in the form of one or more fasteners 223 and internal lumbar supporting features in the form of one or more struts 22 and/or one or more pressure pads 24. FIG. 7A shows a front view of the wetsuit 710. FIG. 7B shows a close-up view of a portion of the wetsuit 710 in FIG. 7A encircled by line 7B-7B.

In some embodiments, the one or more tensioning fasteners 223 can be disposed on the anterior half of the wetsuit 710. In some embodiments, the one or more tensioning fasteners 223 can be disposed on the left and/or right side of the wetsuit 710. The one or more tensioning fasteners 223 can act to tension the lumbar portion 720.

In certain embodiments, the lumbar portion 720 can comprise one or more slots 224. The one or more tensioning fasteners 223 can fasten together the one or more slots 224 in the wetsuit material. In some embodiments, the one or more slots 224 can be surrounded on the interior portion of the wetsuit 710 by one or more pockets 201. In certain embodiments, the one or more pockets 201 comprise a barrier material which prevents water from entering the wetsuit 710. The one or more pockets 201 can function to prevent water from entering the wetsuit 710 when the one or more tensioning fasteners 223 are unfastened. In certain embodiments, a portion of the lumbar portion 720 can connect to the one or more pockets 201. In certain embodiments, a portion of the lumbar portion 720 can connect directly to the one or more tensioning fasteners 223. In certain embodiments, a portion of the lumbar portion 720 can connect directly to the barrier material. In certain embodiments, the one or more straps 23 can connect directly to the one or more tensioning fasteners 223. In certain embodiments, the one or more straps 23 can connect directly to the barrier material.

In certain embodiments, fastening the tensioning fasteners 223 increases the tension in the lumbar portion 720 of the wetsuit 710. In certain embodiments, the one or more pockets 201 are able to stretch out and increase the circumference of the wetsuit 710 when the tensioning fasteners 223 are unfastened. Conversely, the fastening of the tensioning fasteners 223 can cause the slack in the one or more pockets 201 to be taken up. The taking up of slack in the one or more pockets 201 can cause the circumference of the wetsuit 710 to decrease. This decrease can be restricted by the circumference of the person wearing the wetsuit 710. This restriction can cause the components of the lumbar portion 720 to stretch instead of decrease in circumference. This stretching can result in a tension force in the lumbar portion 720 pulling on the one or more tensioning fasteners 223 or the one or more pockets 201. Increasing the tension of the lumbar portion 720 may increase the level of support provided on the lumbosacral or paravertebral area.

Figure 7C:
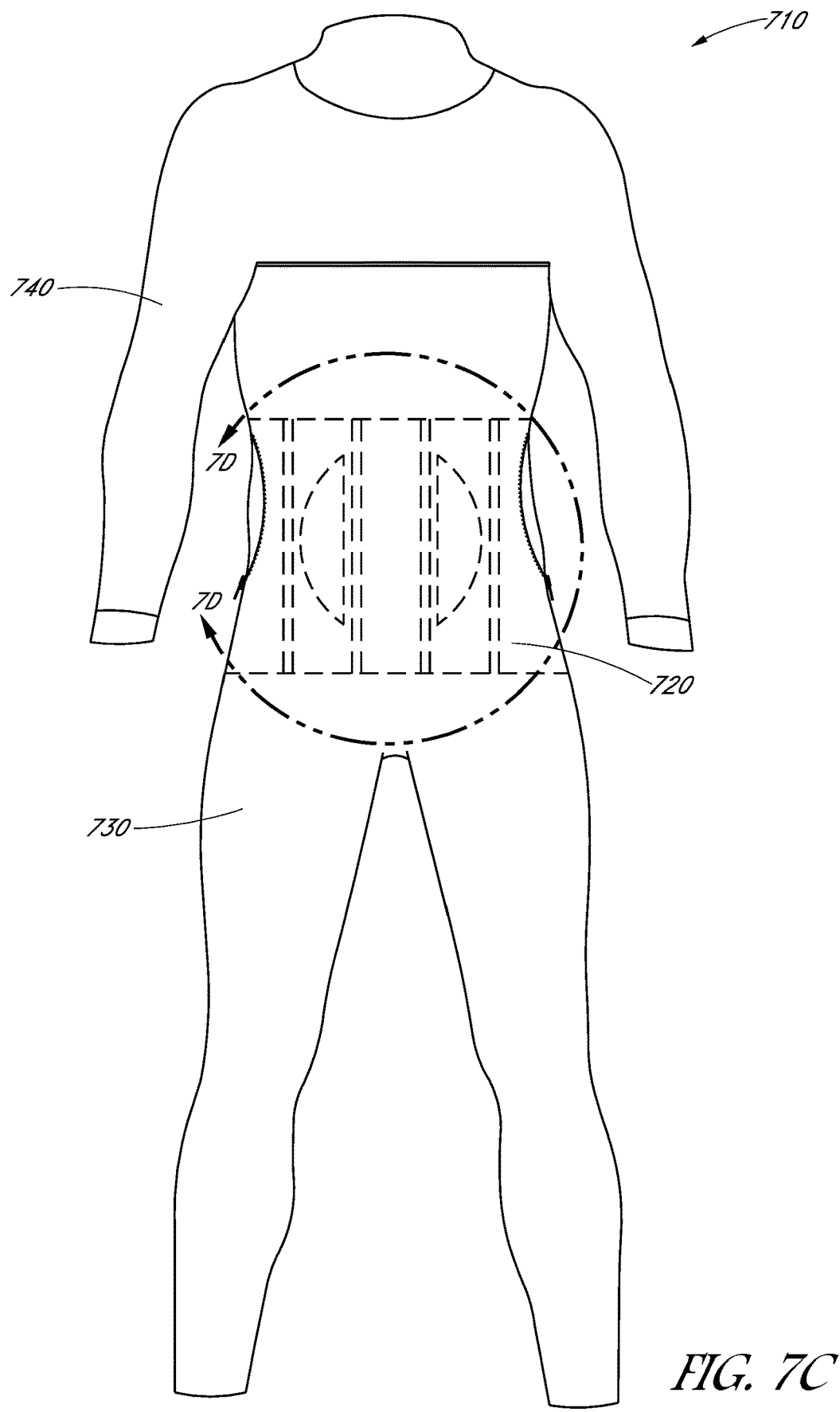
FIG. 7C is a rear view of the wetsuit of FIG. 7A.
Figure 7D:
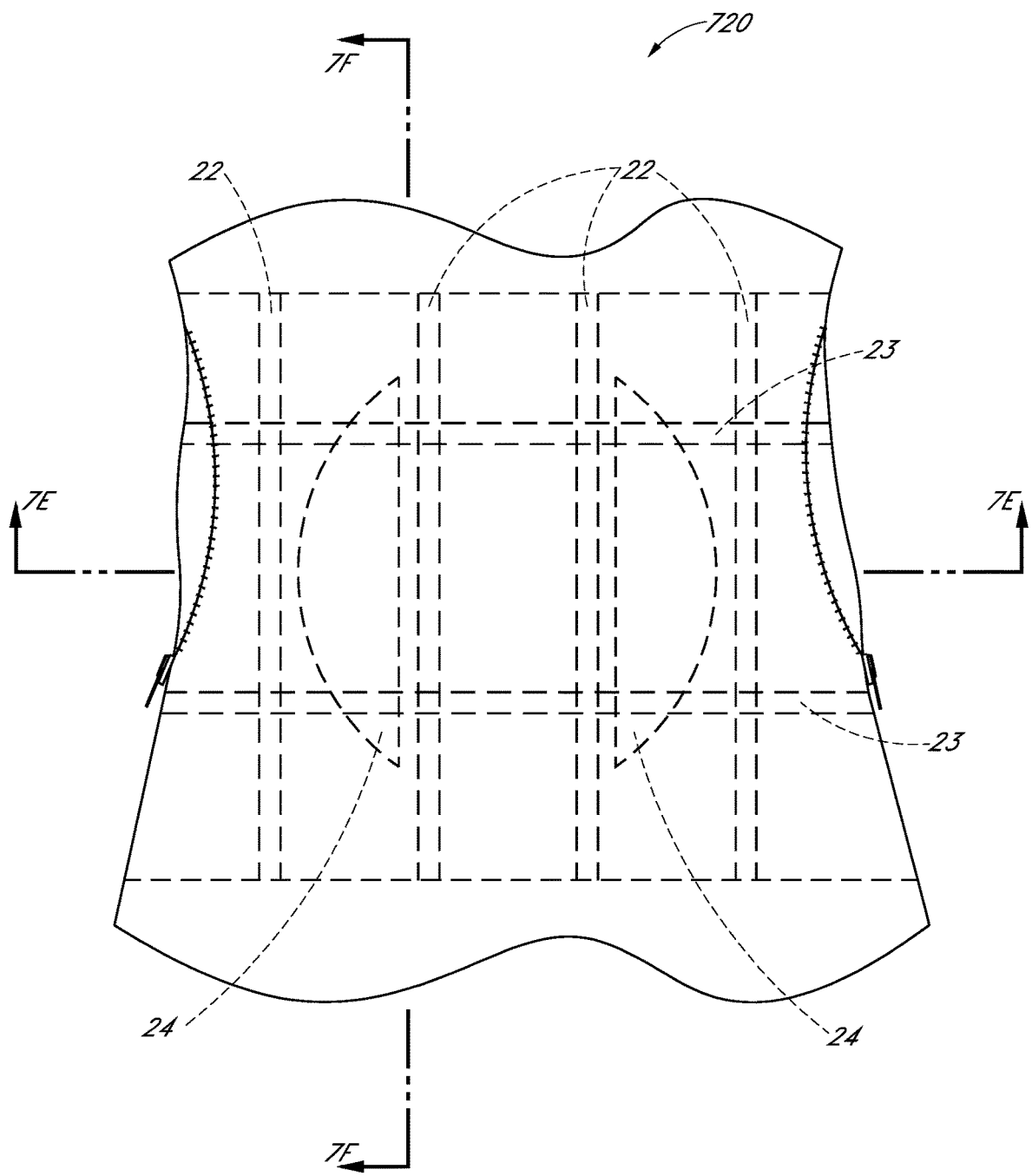
FIG. 7D is a close-up view of the lumbar portion of FIG. 7C encircled by line 7C-7C.

FIG. 7C shows a rear view of the wetsuit 710. FIG. 7D shows a close-up view of the lumbar portion 720 of FIG. 7C encircled by line 7C-7C. In certain embodiments, the lumbar portion 720 comprises the one or more straps 23. In certain embodiments, the lumbar portion 720 comprises a first layer 12a of wetsuit material. In certain embodiments, the lumbar portion 720 comprises a second layer 12b of wetsuit material. In certain embodiments, the first layer 12a of wetsuit material is the inner layer of the lumbar portion 720. In certain embodiments, the second layer 12b of wetsuit material is the outer layer of the lumbar portion 720. In certain embodiments, the one or more straps 23 will be disposed between the first layer 12a of wetsuit material and the second layer 12b of wetsuit material. In certain embodiments, the lumbar portion 720 comprises one or more struts 22. In certain embodiments, the one or more struts 22 will be disposed between the first layer 12a of wetsuit material and the second layer 12b of wetsuit material. In certain embodiments, the lumbar portion 720 comprises one or more pressure pads 24. In certain embodiments, the one or more pressure pads 24 will be disposed between the first layer 12a of wetsuit material and the second layer 12b of wetsuit material. In certain embodiments, the lumbar portion 720 will be disposed on the anterior and posterior portions of the wetsuit 710. In certain embodiments, the lumbar portion 720 will connect to one or more slots 224 on both the anterior and posterior sides of the one or more slots 224. By being disposed on the anterior and posterior portions of the wetsuit 710, the lumbar portion 720 can provide more tension than if it were only on the posterior because the lumbar portion 720 could provide a more rigid anterior portion that does not deform as easily as other wetsuit material would. In certain embodiments, the lumbar portion 720 will encircle the circumference of the wetsuit 710 from anterior to posterior. In certain embodiments, the lumbar portion 720 may only be broken up by vertical slots when viewing the wetsuit 710 from the view of FIG. 7A.

Figure 7E:
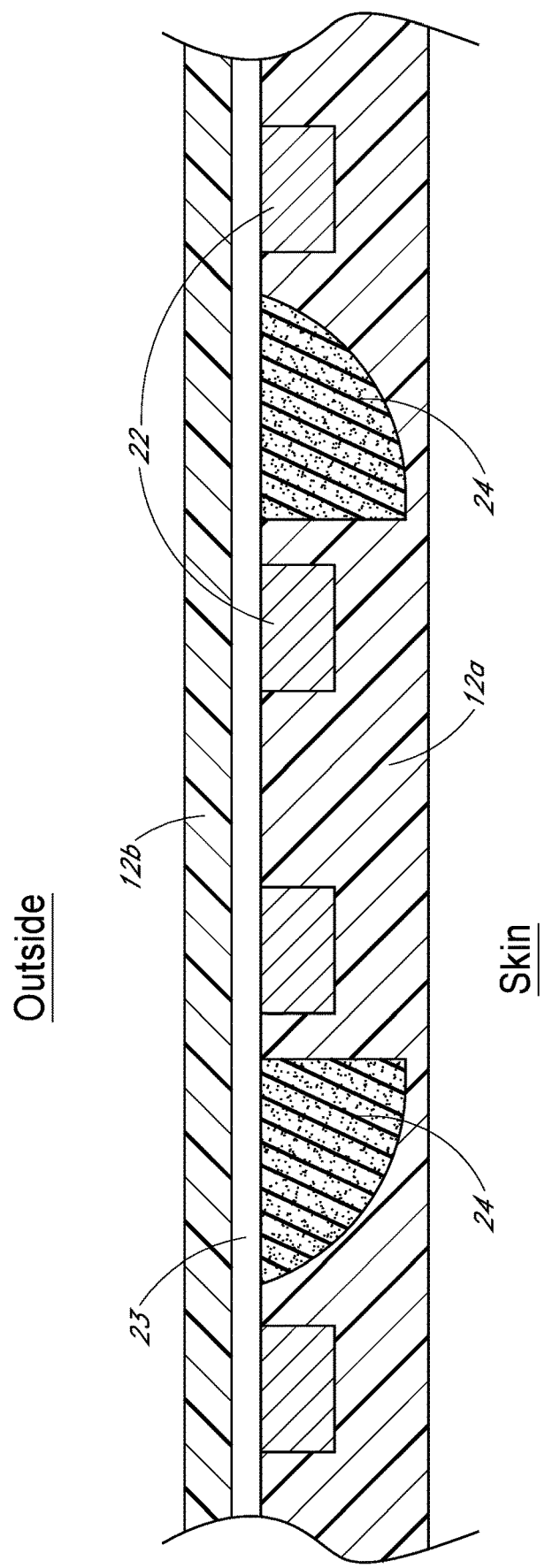
FIG. 7E is a horizontal cross-sectional view through the lumbar portion of FIG. 7D taken at line 7E-7E.
Figure 7F:
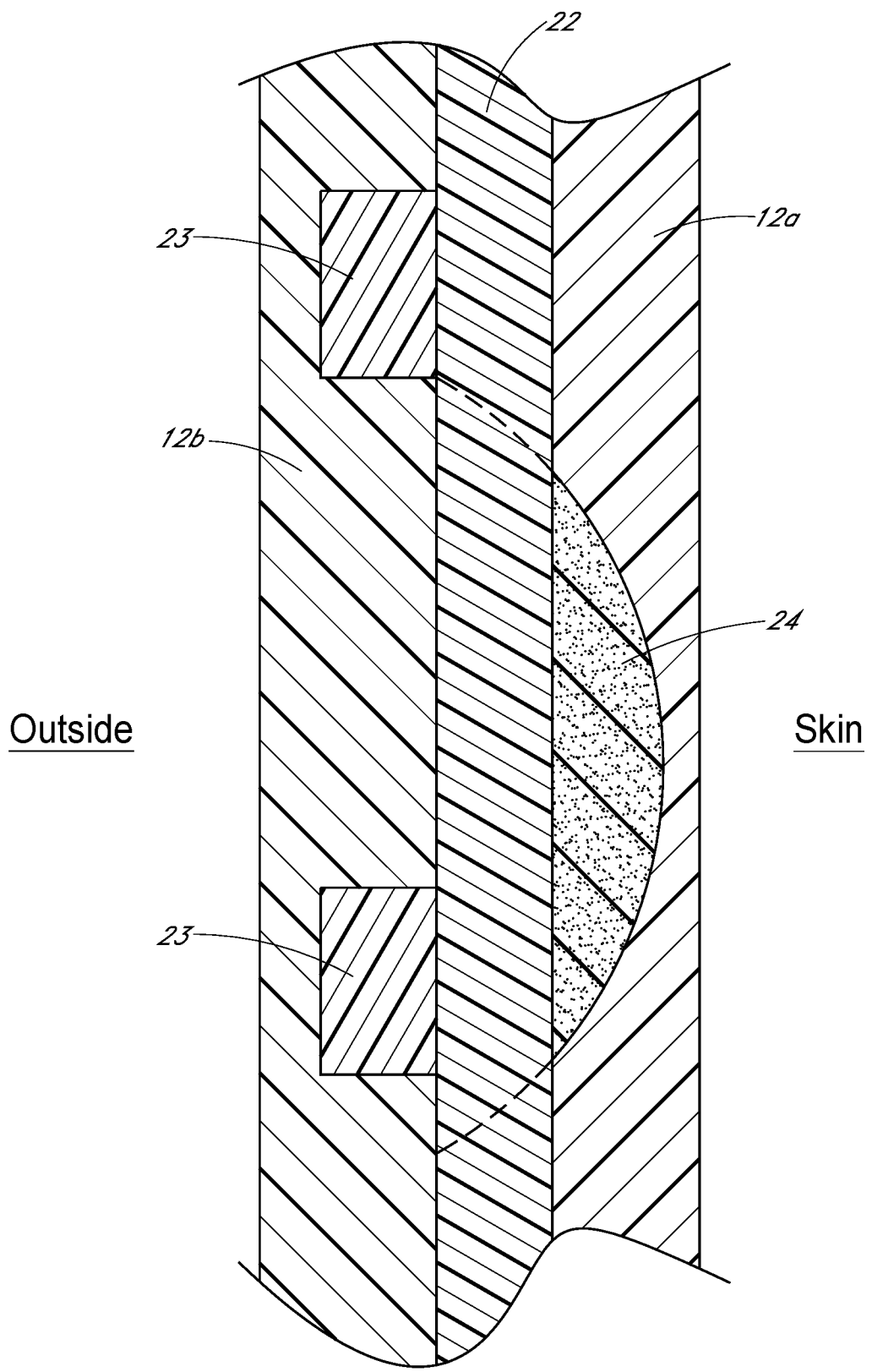
FIG. 7F is a vertical cross-sectional view of the lumbar portion of FIG. 7D taken along line 7F-7F.
Figure 7G:
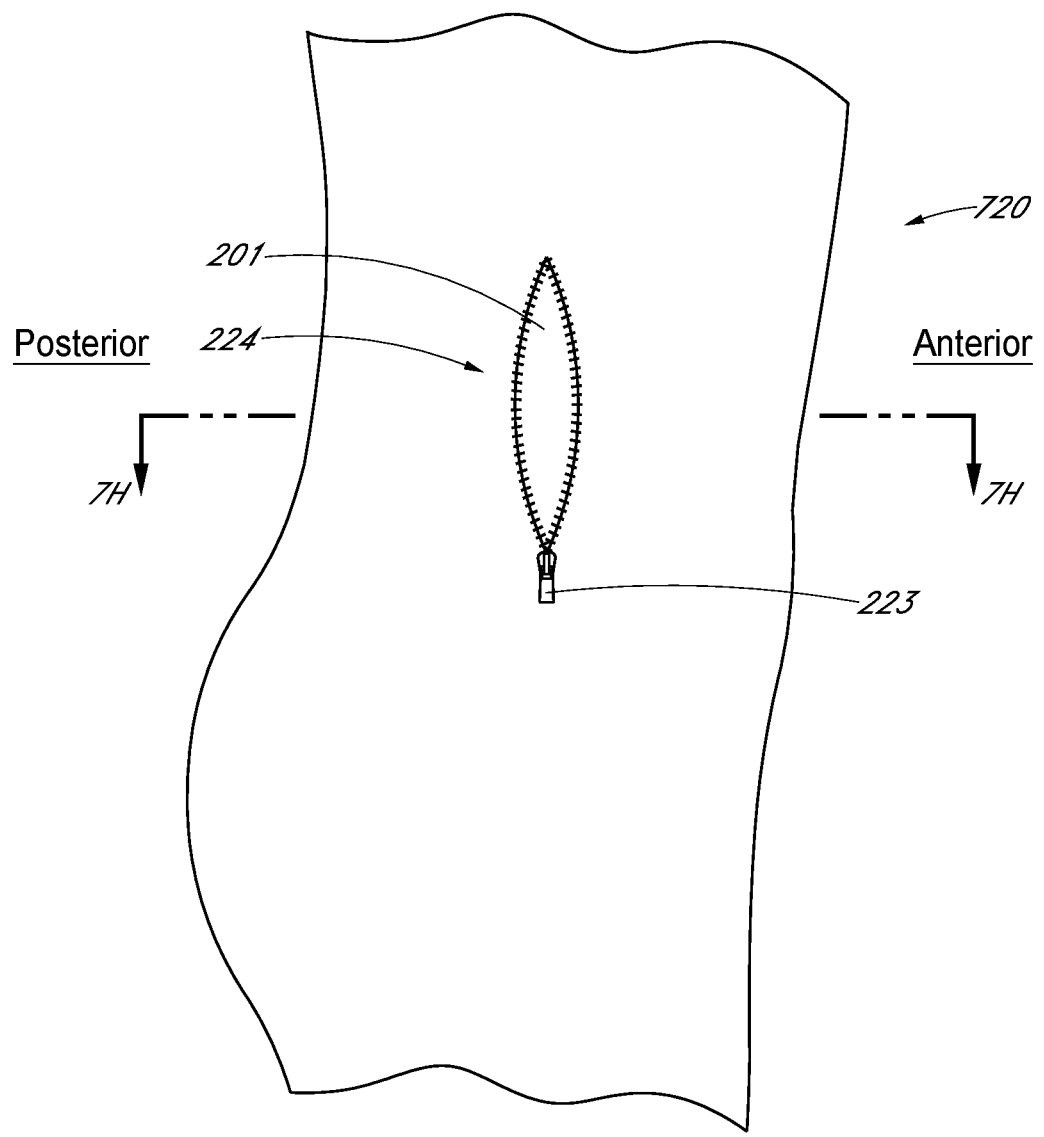
FIG. 7G is a partial right-side view of the lumbar portion of the wetsuit from FIG. 7A.

FIG. 7E shows a horizontal cross-sectional view of the lumbar portion 720 of FIG. 7D taken across the line 7E-7E. FIG. 7F shows a vertical cross-sectional view of the lumbar portion 720 of FIG. 7D taken across the line 7F-7F. FIG. 7G shows a right-side view of the torso portion of a lumbar supportive wetsuit 710. In some embodiments, the right-side view of the wetsuit 710 is substantially symmetrical to the left-side view of the wetsuit 710. FIG. 7G shows a right side view of a wetsuit 710 with a lumbar portion 720 that utilizes tensioning fasteners 223. In some embodiments, the right-side view of the wetsuit 710 is not substantially symmetrical to the left-side view of the wetsuit 710. In certain embodiments, there can be one or more slots 224 on the right-hand and left-hand sides of the lumbar portion 720.

Figure 7H:
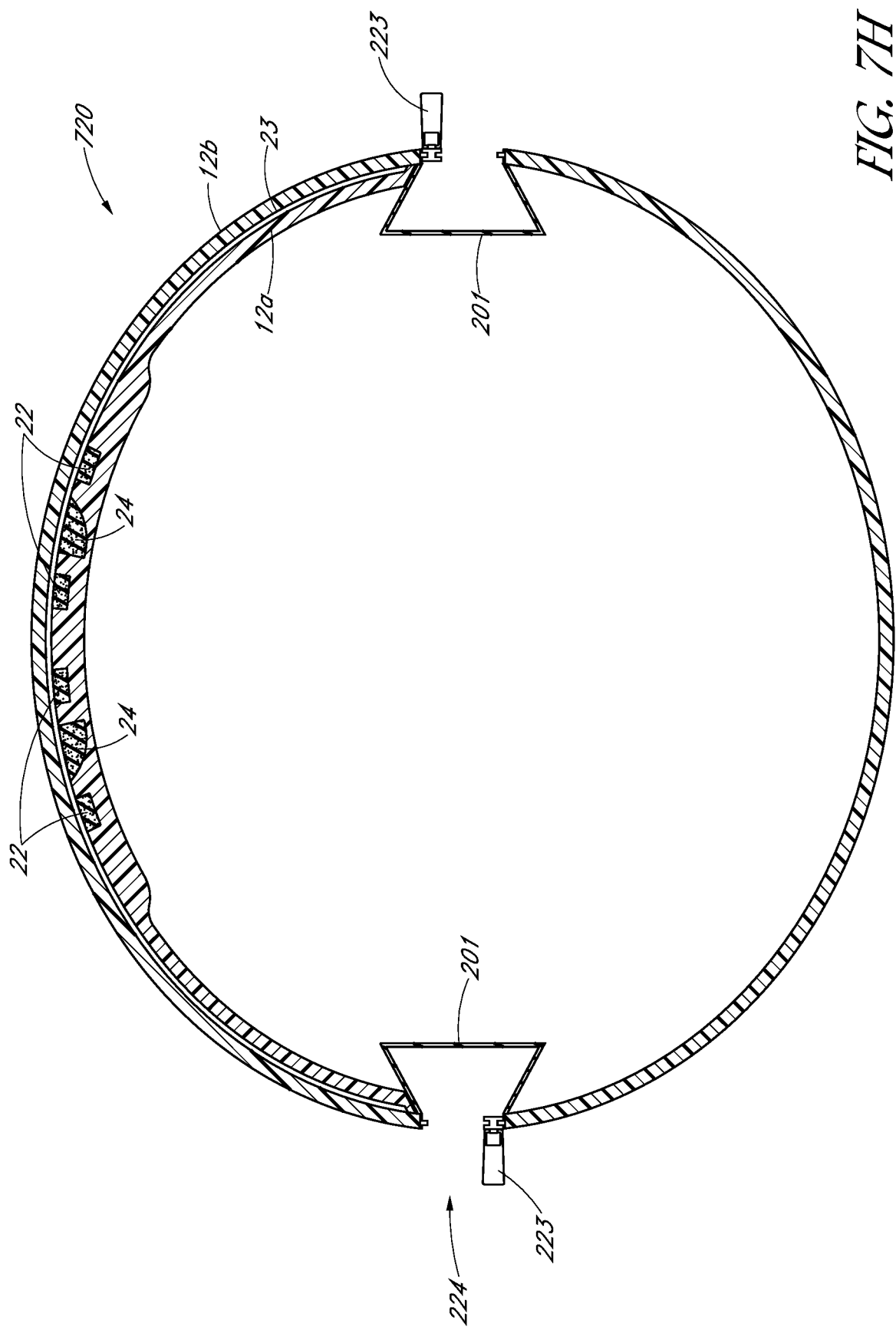
FIG. 7H is a horizontal cross-sectional view of the lumbar portion of FIG. 7G taken across the line 7H-7H.

FIG. 7H shows a horizontal cross-sectional view of the lumbar portion 720 of FIG. 7G taken across the line 7H-7H. The vertical slots 224 can be used to cinch the lumbar portion 720. In embodiments with more than one vertical slot 224, the amount of tension can be adjusted by incrementally fastening some of the tensioning fasteners 223. In certain embodiments, the barrier material 201 can stretch from a first edge of the one or more slots 224 to a second edge. The barrier material 201 can completely surround the interior portion of the opening created by the vertical slot 224 when it is in an open or unfastened position. In certain embodiments, the fastener 223 can be capable of forming a barrier to water entering the wetsuit 710 when it is in a closed or fastened position. In the embodiment illustrated in FIGS. 7A and 7B, the tensioning fasteners 223 are zippers. However, a person of skill in the art will appreciate that there are many other types of tensioning fasteners 223 that could be used. In certain embodiments, one tensioning fastener 223 can be used. In certain embodiments, a plurality of tensioning fasteners 223 can be used. Additionally, the lumbar portion 720 illustrated in FIGS. 7A-7H does not extend across the anterior portion of the wetsuit 710. In certain embodiments, the lumbar portion 720 will be disposed on both the posterior and anterior portions of the wetsuit 710.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A wetsuit that is configured to provide adjustable support to a lumbosacral region of a wearer of the wetsuit, the wetsuit comprising:
 a lumbar portion having at least one layer of foam rubber material and one or more struts disposed under the at least one layer of foam rubber material,
 the lumbar portion configured to extend around the lumbosacral region of the wearer;
 a securement mechanism comprising at least one first part and at least one second part, the at least one first part being configured to be releasably attached to the at least one second part, one of the at least one first part or the at least one second part being a hook type fastener and the other of the at least one first part or the at least one second part being a loop type fastener;
 at least one tensioning mechanism that allows the wearer to selectively change a level of support provided by at least the one or more struts of the lumbar portion to the lumbosacral region of the wearer, wherein the at least one tensioning mechanism is an elastic strap comprising two end portions disposed outside the lumbar portion, wherein the two end portions and an outer front surface of the lumbar portion comprise the securement mechanism, and wherein the level of support is configured to be adjusted by changing a position of one or both of the two end portions on the outer front surface of the lumbar portion;
 one or more pressure pads disposed in the lumbar portion; and
 a layer of nylon laminated on the at least one layer of foam rubber material,
 wherein at least one of the one or more pressure pads is on an outer side or an inner side of at least one of the one or more struts.

2. The wetsuit of claim 1, wherein the one or more struts comprises a high-density polyethylene.

3. The wetsuit of claim 1, wherein the lumbar portion is configured to extend around the entire torso of the wearer.

4. The wetsuit of claim 1, wherein the at least one of the one or more pressure pads is disposed on the outer side of the at least one of the one or more struts.

5. The wetsuit of claim 1, wherein the at least one of the one or more pressure pads is disposed on the inner side of the at least one of the one or more struts.

6. The wetsuit of claim 1, wherein the one or more struts are not directly connected to the at least one tensioning mechanism.

7. A wetsuit that is configured to provide adjustable support to a lumbosacral region of a wearer of the wetsuit, the wetsuit comprising:
 a lumbar portion comprising at least one layer of foam rubber and one or more struts disposed under the at least one layer of foam rubber;

a layer of nylon laminated on the at least one layer of foam rubber;

a securement mechanism comprising at least one first part and at least one second part, the at least one first part being configured to be releasably attached to the at least one second part, one of the at least one first part or the at least one second part being a hook type fastener and the other of the at least one first part or the at least one second part being a loop type fastener;

the lumbar portion configured to extend around at least a portion of a torso of the wearer, the lumbar portion having an elastic strap so that the wearer of the wetsuit can selectively change a level of support provided by at least the one or more struts of the lumbar portion to the lumbosacral region of the wearer, wherein the elastic strap comprises two end portions disposed outside the lumbar portion, wherein the two end portions and an outer front surface of the lumbar portion comprise the securement mechanism, and wherein the level of support is configured to be adjusted by changing a position of one or both of the two end portions on the outer front surface of the lumbar portion; and one or more pressure pads disposed in the lumbar portion, wherein at least one of the one or more pressure pads is on an outer side or an inner side of at least one of the one or more struts.

8. The wetsuit of claim 7, wherein the one or more struts are arranged perpendicular to the elastic strap.

9. The wetsuit of claim 7, wherein a length of the one or more struts is configured to extend across the lumbosacral region of the wearer.

10. The wetsuit of claim 7, wherein the one or more struts are coextensive with a height of the lumbar portion along a vertical axis.

11. The wetsuit of claim 7, wherein the one or more struts comprise a plurality of struts that are spaced apart along a length of the lumbar portion.

12. The wetsuit of claim 7, wherein the one or more struts comprise a high-density polyethylene.

13. The wetsuit of claim 7, wherein the one or more struts are at least in part formed of a material with a tensile strength greater than that of the elastic strap and that of the least one layer of foam rubber.

14. The wetsuit of claim 7, wherein the one or more pressure pads are coextensive with a height of the lumbar portion along a vertical axis.

15. The wetsuit of claim 7, wherein the one or more pressure pads comprise a plurality of pressure pads that are spaced apart along a length of the lumbar portion.

16. The wetsuit of claim 7, wherein the lumbar portion is configured to extend around the entire torso of the wearer.

17. The wetsuit of claim 7, wherein the lumbar portion is embedded within the wetsuit.

18. The wetsuit of claim 7, wherein the lumbar portion is configured to be continuous around the torso.

19. The wetsuit of claim 7, wherein the at least one layer of foam rubber comprises a first layer and a second layer.

20. The wetsuit of claim 7, wherein the at least one of the one or more pressure pads is disposed on the outer side of the at least one of the one or more struts.

21. The wetsuit of claim 7, wherein the at least one of the one or more pressure pads is disposed on the inner side of the at least one of the one or more struts.

22. A wetsuit configured to provide support to a lumbosacral region of a wearer of the wetsuit, the wetsuit comprising a lumbar portion having at least one layer of foam rubber, one or more struts disposed under the at least one layer of foam rubber, a layer of nylon laminated on the at least one layer of foam rubber, a securement mechanism, and an elastic strap, the lumbar portion configured to be disposed at the lumbosacral region of the wearer, the securement mechanism comprising at least one first part and at least one second part, the at least one first part being configured to be releasably attached to the at least one second part, one of the at least one first part or the at least one second part being a hook type fastener and the other of the at least one first part or the at least one second part being a loop type fastener, the elastic strap being configured to allow the wearer of the wetsuit to selectively change a level of support provided by at least the one or more struts of the lumbar portion to the lumbosacral region of the wearer, wherein the elastic strap comprises two end portions disposed outside the lumbar portion, wherein the two end portions and an outer front surface of the lumbar portion comprise the securement mechanism, and wherein the level of support is configured to be adjusted by changing a position of one or both of the two end portions on the outer front surface of the lumbar portion; and one or more pressure pads disposed in the lumbar portion, wherein at least one of the one or more pressure pads is on an outer side or an inner side of at least one of the one or more struts.

23. The wetsuit of claim 22, wherein the at least one of the one or more pressure pads is disposed on the outer side of the at least one of the one or more struts.

24. The wetsuit of claim 22, wherein the at least one of the one or more pressure pads is disposed on the inner side of the at least one of the one or more struts.

* * * * *